US009492466B2

(12) United States Patent
De La Cruz Cordero et al.

(10) Patent No.: US 9,492,466 B2
(45) Date of Patent: Nov. 15, 2016

(54) BETA-HYDROXY-GAMMA-AMINOPHOSPHONATES FOR TREATING IMMUNE DISORDERS

(71) Applicant: Nucitec S.A. de C.V., Queretaro (MX)

(72) Inventors: Ricardo Abraham De La Cruz Cordero, Huixtla (MX); Jorge Luis Rosado Loria, Queretaro (MX); Miguel Angel Duarte Vazquez, Irapuato (MX); José Mario Ordóñez Palacios, Cuernavaca (MX); Jorge Alberto Reyes Esparza, Mexico City (MX); Maria de Lourdes Rodriguez Fragoso, Mexico City (MX)

(73) Assignee: Nucitec S.A. de C.V., Queretaro (MX)

( * ) Notice: Subject to any disclaimer, the term of this patent is extended or adjusted under 35 U.S.C. 154(b) by 262 days.

(21) Appl. No.: 13/826,951

(22) Filed: Mar. 14, 2013

(65) Prior Publication Data

US 2014/0107079 A1   Apr. 17, 2014

Related U.S. Application Data

(60) Provisional application No. 61/659,700, filed on Jun. 14, 2012.

(51) Int. Cl.
| | |
|---|---|
| A61K 31/662 | (2006.01) |
| C07F 9/38 | (2006.01) |
| C07F 9/40 | (2006.01) |
| A61K 45/06 | (2006.01) |

(52) U.S. Cl.
CPC ............ *A61K 31/662* (2013.01); *A61K 45/06* (2013.01); *C07F 9/3808* (2013.01); *C07F 9/3834* (2013.01); *C07F 9/4006* (2013.01)

(58) Field of Classification Search
None
See application file for complete search history.

(56) References Cited

U.S. PATENT DOCUMENTS

| | | |
|---|---|---|
| 6,444,701 B1 | 9/2002 | Giannessi et al. |
| 8,178,515 B2 | 5/2012 | De La Cruz Cordero et al. |
| 8,536,362 B2 | 9/2013 | De La Cruz Cordero et al. |
| 2003/0162754 A1 | 8/2003 | Ligon |
| 2007/0207983 A1 | 9/2007 | Nieuwenhuizen et al. |
| 2010/0087400 A1* | 4/2010 | De La Cruz Cordero et al. ........................ 514/114 |

FOREIGN PATENT DOCUMENTS

| | | |
|---|---|---|
| FR | 1543469 | 10/1968 |

OTHER PUBLICATIONS

"Autoimmune Diseases" from the Health Central Network. (20009).*

De la Cruz-Cordero, R. et al., "Preparation of phosphostatine and phosphoepistatine from L-leucine via high diastereoselective reduction of 3-amino-2-ketophosphonates," *ARKIVOC* (vi):277-286, ARKAT USA, Inc. (2005).
Deems, R.O. et al., "Hypoglycemic effects of a novel fatty acid oxidation inhibitor in rats and monkeys," *Am. J Physiol. Regul. Integr. Comp. Physiol.* 274:R524-R528, American Physiological Society (1998).
Foley, J.E., "Rationale and Application of Fatty Acid Oxidation Inhibitors in Treatment of Diabetes Mellitus," *Diabetes Care* 15:773-784, American Diabetes Association (1992).
Gómez-Solís, A. et al., "Efficacy and Safety of Two Analogs of L-Carnitine on Rats Made Insulin Resistant by a High-Fructose Diet," *Pharmacol.* 88:1-8, S. Karger AG, Basel (2011).
Mikolajczyk, M. et al., "Chemoenzymatic Synthesis of Phosphocarnitine Enantiomers," *J. Org. Chem.* 67:7872-7875, American Chemical Society (2002).
Ordóñez, M. and Cativiela, C., "Stereoselective synthesis of γ-amino acids," *Tetrahedron Asymmetry* 18:3-99, Elsevier Ltd. (2007).
Stahl, R.H. and Wermuth, C.G., Eds., *Handbook of Pharmaceutical Salts: Properties, Selection, and Use*, pp. 1-7, 84, 161-173, 214-215, 310-311, Wiley-VCH (2002).
Wang, K. et al., "Enzymatic synthesis of phosphocarnitine, phosphogabob and fosfomycin," *Org. Biomol. Chem.* 1: 3564-3569, The Royal Society of Chemistry (2003).
Wróblewski, A.E. and Halajewska-Wosik, A., "An Efficient Synthesis of Enantiomeric (S)-Phosphocarnitine," *Eur. J. Org. Chem.* 16: 2758-2763, Wiley-VCH Verlag GmbH, Weinheim (2002).
Yamagishi, T. et al., "Asymmetric synthesis of phosphonic acid analogues for acylcarnitine," *Tetrahedron* 62:54-65, Elsevier Ltd. (2006).
Office Action mailed Oct. 25, 2011, in U.S. Appl. No. 12/575,856, filed Oct. 8, 2009 (now U.S. Pat. No. 8,536,362 B2), inventors: De La Cruz Cordero et al., U.S. Patent and Trademark Office, Alexandria, VA.
Abdulahad, W.H. et al., "Functional Defect of Circulating Regulatory CD4+ T Cells in Patients With Wegener's Granulomatosis in Remission," *Arthritis & Rheumatism* 56:2080-2091, American College of Rheumatology (2007).
Alzabin, S. and Williams, R.O., "Effector T cells in rheumatoid arthritis: Lessons from animal models," *FEBS Lett.* 585:3649-3659, Elsevier B.V. (2011).
Barnett, A.J. et al., "T lymphocyte subset abnormalities and HLA antigens in scleroderma (systemic sclerosis)," *Clin. Exp. Immunol.* 76:24-29, Blackwell Scientific Publications (1989).
Bennett, J.C., "The Role of T Lymphocytes in Rheumatoid Arthritis and Other Autoimmune Diseases," *Arthritis Rheum.* 58:S53-S57, American College of Rheumatology (2008).
Berden, A.E. et al., "Cellular Immunity in Wegener's Granulomatosis," *Arthritis Rheum.* 60:1578-1587, American College of Rheumatology (2009).

(Continued)

*Primary Examiner* — Bong-Sook Baek
(74) *Attorney, Agent, or Firm* — Sterne, Kessler, Goldstein & Fox P.L.L.C.

(57) ABSTRACT

The present disclosure provides methods of treating, ameliorating, or preventing immune disorders, allergic disorders, or inflammatory disorders, or combinations thereof, or providing hepatoprotection in subject. In one aspect, the method comprises administering to a subject a therapeutically effective amount of a β-hydroxy-γ-aminophosphonate or β-amino-γ-aminophosphonate.

10 Claims, 17 Drawing Sheets

(56) References Cited

OTHER PUBLICATIONS

Bhatia, R. et al., "Lymphocyte Subsets in Acute Rheumatic Fever and Rheumatic Heart Disease," *Clin. Cardiol.* 12:34-38, John Wiley & Sons, Inc. (1989).

Bulletti, C. et al., "Reproductive failure due to spontaneous abortion and recurrent miscarriage," *Hum. Reprod. Update* 2:118-136, European Society for Human Reproduction and Embryology (1996).

Cai, Y. et al., "New insights of T cells in the pathogenesis of psoriasis," *Cell. Mol. Immunol.* 9:302-309, CSI and USTC (2012).

Chadebech, P. et al., "IgA-mediated human autoimmune hemolytic anemia as a result of hemagglutination in the spleen, but independent of complement activation and FcαRI," *Blood* 116:4141-4147, The American Society of Hematology (2010).

Chistiakov, D.A., "Immunogenetics of Hashimoto's thyroiditis," *J. Autoimmune Dis.* 2:21 pages, BioMed Central Ltd. (2005).

Colombo, M. et al., "T and B lymphocytes in patients with chronic active hepatitis (CAH)," *Clin. Exp. Immunol.* 30:4-9, Blackwell Scientific Publications (1977).

Cope, A.P. et al., "The central role of T cells in rheumatoid arthritis," *Clin. Exp. Rheumatol.* 25(Suppl. 46):S-4-S11, Clinical and Experimental Rheumatology (2007).

Costello, P.J. et al., "Psoriatic Arthritis Joint Fluids Are Characterized by CD8 and CD4 T Cell Clonal Expansions that Appear Antigen Driven," *J. Immunol.* 166:2878-2886, The American Association of Immunologists (2001).

Dalakas, M.C. and Hohlfeld, R., "Polymyositis and dermatomyositis," *The Lancet* 362:971-982, Lancet Publishing Group (2003).

Deschènes, J. et al., "Activated T lymphocytes in uveitis," *Br. J. Ophthalmol.* 72:83-87, BMJ Pub. Group (1988).

Dornmair, K. et al., "T-Cell-Mediated Autoimmunity: Novel Techniques to Characterize Autoreactive T-Cell Receptors," *Am. J. Pathol.* 163:1215-1226, American Society for Investigative Pathology (2003).

Duftner, C. et al., "Prevalence, clinical relevance and characterization of circulating cytotoxic CD4+CD28− T cells in ankylosing spondylitis," *Arthritis Res. Ther.* 5:R292-R300, BioMed Central Ltd. (2003).

Dworkin, M.S. et al., "Reactive Arthritis and Reiter's Syndrome Following an Outbreak of Gastroenteritis Caused by *Salmonella enteritidis,*" *Clin. Infect. Dis.* 33:1010-1014, Infectious Diseases Society of America (2001).

Fasth, A.E.R. et al., "T Cell Infiltrates in the Muscles of Patients with Dermatomyositis and Polymyositis Are Dominated by $CD28^{null}$ T Cells," *J. Immunol.* 183:4792-4799, The American Association of Immunologists, Inc. (2009).

Ferran, M.F. and Santamaria-Babi, L.F., "Pathological Mechanisms of Skin Homing T Cells in Atopic Dermatitis," *WAO Journal* 3:44-47, World Allergy Organization (2010).

Fletcher, J.M. et al., "T cells in multiple sclerosis and experimental autoimmune encephalomyelitis," *Clin. Exp. Immunol.* 162:1-11, Br. Society for Immunology (2010).

Freeman, M. and Weetman, A.P., "T and B cell reactivity to adrenal antigens in autoimmune Addison's disease," *Clin. Exp. Immunol.* 88:275-279, Br. Society for Immunology (1992).

Ghaly, N.R. et al., "Role of mast cells and T-lymphocytes in pemphigus vulgaris: significance of CD44 and the c-kit gene product (CD117)" *Eastern Mediterranean Health Journal* 11:1009-1017, Eastern Mediterranean Regional Office of the World Health Organization (2005).

Gianfrani, C. et al., "Celiac Disease Association with CD8+ T Cell Responses: Identification of a Novel Gliadin-Derived HLA-A2-Restricted Epitope," *J. Immunol.* 170:2719-2726, The American Association of Immunologists (2003).

Giurdanella, F. et al., "A Possible Role for CD8+ Lymphocytes in the Cell-Mediated Pathogenesis of Pemphigus Vulgaris," *Mediators of Inflamm.* 2013:1-35, Hindawi Publishing Corporation (2013).

Gravano, D.M. and Hoyer, K.K., "Promotion and prevention of autoimmune disease by CD8+ T cells," *J. Autoimmun.* 2013:1-12, Elsevier Ltd. (2013).

Grunewald, J. and Eklund, A., "Role of $CD4^+$ T Cells in Sarcoidosis," *Proc. Am. Thorac. Soc.* 4:461-464, American Thoracic Society (2007).

Grunewald, J. et al., "T-Cell Expansions With Conserved T-Cell Receptor β Chain Motifs in the Peripheral Blood of HLA-DRB1*0401 Positive Patients With Necrotizing Vasculitis," *Blood* 92:3737-3744, The American Society of Hemotology (1998).

Hohlfeld, R. et al., "Polymyositis Mediated by T Lymphocytes That Express the γ/δReceptor," *N. Engl. J. Med.* 324:877-881, Massachusetts Medical Society (1991).

Homann, D. et al., "Autoreactive $CD4^+$ T Cells Protect from Autoimmune Diabetes via Bystander Suppression Using the IL-4/Stat6 Pathway," *Immunity* 11:463-472, Cell Press (1999).

Iwona, B.-S., "Graves' Disease—The Interaction of Lymphocytes and Thyroid Cells," in *Autoimmune Disorders—Pathogenetic Aspects*, Mavragani, C.P., ed., Ch. 12, pp. 229-240, InTech (2011).

Iwona, B.-S., "Hashimoto's Thyroiditis—Interactions of Lymphocytes, Thyroid Cells and Fibroblasts," in *Autoimmune Disorders—Pathogenetic Aspects*, Mavragani, C.P., ed., Ch. 13, pp. 241-254, InTech (2011).

Jimemez, S.A. and Derk, C.T., "Following the Molecular Pathways toward an Understanding of the Pathogenesis of Systemic Sclerosis," *Ann. Intern. Med.* 140:37-50, American College of Physicians (2004).

Jin, J.-O. and Yu, Q., "T Cell-Associated Cytokines in the Pathogenesis of Sjögren's Syndrome," *J. Clin. Cell. Immunol.* S!(9):1-14, OMICS Publishing Group (2013).

Kahan, A. et al., "Abnormalities of T lymphocyte subsets in systemic sclerosis demonstrated with anti-CD45RA and anti-CD29 monoclonal antibodies," *Ann. Rheum. Dis.* 50:354-358, BMJ Pub. Group (1991).

Kalha, I. and Sellin, J.H., "Common Variable Immunodeficiency and the Gastrointestinal Tract," *Curr. Gastroenterol. Rep.* 6:377-383, Current Science Inc. (2004).

Kasper, L.H. et al., "Regulatory mechanisms of the immune system in multiple sclerosis. T regulatory cells: turned on to turn off," *J. Neurol.* 254(Suppl 1):1/10-1/14, Springer-Verlag (2007).

Kasperkiewicz, M. and Zillikens, D., "The Pathophysiology of Bullous Pemphigoid," *Clinic. Rev. Allerg. Immunol.* 33:67-77, Humana Press Inc. (2007).

Kawanami, S. et al., "Lymphocyte function in myasthenia gravis," *J. Neurol. Neurosurg. Psychiatr.* 42:734-740, BMJ Pub. Group (1979).

Kennedy, R. et al., "Activated T cells in Graves' disease before treatment," *Clin. Exp. Immunol.* 59:377-382, Blackwell Scientific Publications (1985).

Kivisäkk, P. et al., "Localizing CNS immune surveillance: Meningeal APCs activate T cells curing EAE," *Ann. Neurol.* 65:457-469, Wiley-Liss (2009).

Kotlan, B. et al., "High anti-paternal cytotoxic T-lymphocyte precursor frequencies in women with unexplained recurrent spontaneous abortions," *Hum. Reprod.* 16:1278-1285, European Society of Human Reproduction and Embryology (2001).

Lima, H.C., "Role of regulatory T cells in the development of skin diseases," *An. Bras. Dermatol.* 81:269-281, Anais Brasileiros de Dermatologia (2006).

Markovic-Plese, S. et al., "The initiation of the autoimmune response in multiple sclerosis," *Clin. Neurol. Neurosurg.* 2004:1-5, Elsevier B.V. (2004).

Mazziotti, G. et al., "Type-1 response in peripheral $CD4^+$ and $CD8^+$ T cells from patients with Hashimoto's thyroiditis," *Eur. J. Endocrinol.* 148:383-388, Society of the European Journal of Endocrinology (2003).

Melms, A. et al., "Thymus in Myasthenia Gravis: Isolation of T-Lymphocyte Lines Specific for the Nicotinic Acetylcholine Receptor from Thymuses of Myasthenic Patients," *J. Clin. Invest.* 81:902-908, The American Society for Clinical Investigation, Inc. (1988).

(56) References Cited

OTHER PUBLICATIONS

Morimoto, C. et al., "Abnormalities in CD4+ T-Lymphocyte Subsets in Inflammatory Rheumatic Diseases," *Am. J. Med.* 84:817-825, Excerpta Medica, New York (1988).

Nordström, D. et al., "Synovial fluid cells in Reiter's syndrome," *Ann. Rheum. Dis.* 44:852-856, BMJ Pub. Group (1985).

Oh, H.-M. et al., "Autoreactive Memory CD4+ T Lymphocytes That Mediate Chronic Uveitis Reside in the Bone Marrow through STAT3-Dependent Mechanisms," *J. Immunol.* 187:3338-3346, The American Association of Immunologists, Inc. (2011).

Owen, D.A., "Gastritis and Carditis," *Modern Pathol.* 16:325-341, The United States and Canadian Academy of Pathology, Inc. (2003).

Rossi, G.A. et al., "Pulmonary sarcoidosis: excess of helper T lymphocytes and T cell subset imbalance at sites of disease activity," *Thorax* 39:143-149, British Medical Association (1984).

Sanchez-Tapias, J. et al., "Lymphocyte populations in liver biopsy specimens from patients with chronic liver disease," *Gut* 18:472-475, BMJ Pub. Group (1977).

Schirmer, M. et al., "Circulating cytotoxic CD8+ CD28- T cells in ankylosing spondylitis," *Arthritis Res.* 4:71-76, BioMed Central Ltd. (2002).

Shinjo, S.K. et al., "Dermatomyositis and polymyositis: from immunopathology to immunotherapy (immunobiologics)," *Rev. Bras. Reumatol.* 53:101-110, Elsevier Editora Ltda. (2013).

Si, L. et al., "T-Lymphocytes Subsets in Liver Tissues of Patients with Primary Biliary Cirrhosis (PBC), Patients with Primary Sclerosing Cholangitis (PSC) and Normal Controls," *J. Clin. Immunol.* 4:262-272, Plenum Publishing Corporation (1984).

Sollid, L.M., "Molecular Basis of Celiac Disease," *Annu. Rev. Immunol.* 18:53-81, Annual Reviews, Inc. (2000).

Stinissen, P. and Hellings, N., "Activation of myelin reactive T cells in multiple sclerosis: A possible role for T cell degeneracy?," *Eur. J. Immunol.* 38:1190-1193, Wiley-VCH Verlag GmbH & Co. KGaA, Weinheim (2008).

Sun, Q. et al., "An aggressive systematic strategy for acute respiratory distress syndrome caused by severe pneumonia after renal transplantation," *Transpl. Int.* 19:110-116, European Society for Organ Transplantation (2006).

Szalay, B. et al., "Adaptive Immunity in Ankylosing Spondylitis: Phenotype and Functional Alterations of T-Cells before and during Infliximab Therapy," *Clin. Dev. Immunol.* 2012:1-8, Hindawi Publishing Corporation (2012).

Takahashi, H. et al., "Desmoglein 3—specific CD4+ T cells induce pemphigus vulgaris and interface dermatitis in mice," *J. Clin. Invest.* 121:3677-3688, American Society for Clinical Investigation (2011).

Tipping, P.G. and Holdsworth, S.R., "T Cells in Crescentic Glomerulonephritis," *J. Am. Soc. Nephrol.* 17:1253-1263, American Society of Nephrology (2006).

Torres, M.J. et al., "Circulating CLA+ lymphocytes from children with atopic dermatitis contain an increased percentage of cells bearing staphylococcal-related T-cell receptor variable segments," *Clin. Exp. Allergy* 28:1264-1272, Blackwell Science Ltd. (1998).

Vaidya, B. et al., "The cytotoxic T lymphocyte antigen-4 is a major Graves' disease locus," *Hum. Mol. Genet.* 8:1195-1199, Oxford University Press (1999).

Van Alderwegen, I.E. et al., "T cell subsets in immunologically-mediated glomerulonephritis," *Histol. Histopathol.* 12:241-250, Histology and Histopathology, Spain (1997).

Vargas, J.A. et al., "Functional defect of T cells in autoimmune gastritis," *Gut* 36:171-175, British Medical Association (1995).

Wands, J.R. and Isselbacher, K.J., "Lymphocyte Cytotoxicity to Autologous Liver Cells in Chronic Active Hepatitis," *Proc. Natl. Acad. Sci. USA* 72:1301-1303, National Academy of Sciences (1975).

Wang, Y. et al., "CD8+ T Cells Mediate Recovery and Immunopathology in West Nile Virus Encephalitis," *J. Virol.* 77:13323-13334, American Society for Microbiology (2003).

Wilde, B. et al., "T cells in ANCA-associated vasculitis: what can we learn from lesional versus circulating T cells?," *Arthritis Res. Ther.* 12:1-9, BioMed Central Ltd. (2010).

Wong, H.K. et al., "Abnormal NJ-κB Activity in T Lymphocytes from Patients with Systemic Lupus Eythematosus Is Associated with Decreased p65-RelA Protein Expression," *J. Immunol.* 163:1682-1689,The American Association of Immunologists (1999).

Yang, G.-X. et al., "CD8 T Cells Mediate Directed Biliary Ductule Damage in Nonobese Diabetic Autoimmune Biliary Disease," *J. Immunol.* 186:1259-1267, The American Association of Immunologists, Inc. (2011).

Dejaco, C. et al., "Imbalance of regulatory T cells in human autoimmune diseases," *Immunology* 117:289-300, Blackwell Publishing Ltd. (2005).

Abd-Allah, A.R.A. et al., "Pro-inflammatory and oxidative stress pathways which compromise sperm motility and survival may be altered by L-carnitine," *Oxid. Med. Cell. Longev.*2:73-81, Landes Bioscience (2009).

Arafa, H.M.M. et al., "Immunomodulatory effects of L-carnitine and q10 in mouse spleen exposed to low-frequency high-intensity magnetic field," *Toxicology* 187:171-181, Elsevier Science Ltd. (2003).

Gasbarrini, G. et al., "Effects of propionyl-L-carnitine topical irrigation in distal ulcerative colitis: a preliminary report," *Hepatogastroenterology* 50:1385-1389, H.G.E. Update Medical Publishing, Athens (2003).

Idrovo, J.-P. et al., "Stimulation of Carnitine Palmitoyltransferase 1 Improves Renal Function and Attenuates Tissue Damage after Ischemia/Reperfusion," *J. Surg. Res.* 177:157-164, Elsevier Inc. (2012).

Merra, G. et al., "Propionyl-L-carnitine hydrochloride for treatment of mild to moderate colonic inflammatory bowel diseases," *World J. Gastroenterol.* 18:5065-5071, Baishideng Publishing Group (2012).

\* cited by examiner

Fig. 17
Mycetoma induced in mouse
50 mg/kg
5 mg/kg

BETA-HYDROXY-GAMMA-AMINOPHOSPHONATES FOR TREATING IMMUNE DISORDERS

BACKGROUND OF THE DISCLOSURE

1. Field of the Disclosure

This disclosure is in the fields of medicine and immunology. The disclosure provides methods of treating, ameliorating, or preventing diseases or disorders responsive to the number of T-lymphocytes in a subject, and methods of providing hepatoprotection in a subject, comprising administering a therapeutically effective amount of a β-hydroxy-γ-aminophosphonate or β-amino-γ-aminophosphonate to the subject. Diseases and disorders responsive to the number of T-lymphocytes in a subject include immune disorders, allergic disorders, and inflammatory disorders, or combinations thereof.

2. Related Art

Autoimmune and inflammatory diseases affect more than fifty million Americans. The immune system functions as the body's major defense against diseases caused by invading organisms. This complex system fights disease by killing invaders such as bacteria, viruses, parasites or cancerous cells while leaving the body's normal tissues unharmed. The immune system's ability to distinguish the body's normal tissues, or self, from foreign or cancerous tissue, or non-self, is an essential feature of normal immune system function. A second essential feature is memory, the ability to remember a particular foreign invader and to mount an enhanced defensive response when the previously encountered invader returns. The loss of recognition of a particular tissue as self and the subsequent immune response directed against that tissue produce serious illness.

Inflammation is involved in a large number of physiological and pathological conditions affecting animals and humans. Inflammatory responses can usually be traced to an immune response to an antigen, allergen, irritant, endotoxin, or to tissue damage. The process is complex, involving a large number of components, many of which display pleiotropic effects, many of which are amplifiers or inhibitors of other components. While many instances of an inflammatory response are well-controlled and self-limited, many pathologic conditions arise from uncontrolled or inappropriate responses, resulting in both acute and chronic conditions.

The immune system when operating normally is involved in precise functions such as recognition and memory of, specific response to, and clearance of, foreign substances (chemical and cellular antigens) that either penetrate the protective body barriers of skin and mucosal surfaces (transplanted tissue and microorganisms such as bacteria, viruses, parasites) or arise de novo (malignant transformation). The arsenal of the immune response is composed of two major types of lymphocytes that are either B-lymphocytes (B cells, responsible for producing antibodies which attack the invading microorganisms) or the T-lymphocytes (T cells, responsible for eliminating the infected or abnormal target cells) in cooperation with macrophages.

An autoimmune disease results from an inappropriate immune response directed against a self antigen (an autoantigen), which is a deviation from the normal state of self-tolerance. Self-tolerance arises when the production of T cells and B cells capable of reacting against autoantigens has been prevented by events that occur in the development of the immune system during early life. Several mechanisms are thought to be operative in the pathogenesis of autoimmune diseases, against a backdrop of genetic predisposition and environmental modulation There is at present no cure for autoimmune diseases. However, there are a number of traditional approaches to treating autoimmune-related disorders and cancers that are known in the art. Immune responses to therapeutic agents are wide ranging, and can be directed against agents that are both non-human and human in origin. These responses include those that elicit a weak clinical effect and those that limit efficacy which can occasionally result in morbidity or even mortality in subjects. In particular, serious complications can arise with the production of neutralizing antibodies, especially when they target recombinant self proteins and therefore have the potential to cross react with the subject's own endogenous protein (Lim, *Hematology* 10:255-259 (2005)). Problems associated with immunogenicity to biologics, especially monoclonal antibodies, have been reduced largely due to advances in molecular biology. There are, however, many recombinant protein biologics that are identical to endogenously expressed human sequences that still elicit potent neutralizing immune responses in subjects (Hochuli, *J. Interferon Cytokine Res.* 17 Suppl. 1:S15-21 (1997); Schellekens et al., *J. Interferon Cytokine Res.* 17 Suppl. 1:S5-S8 (1997); Namaka et al., *Curr. Med. Res. Opin.* 22:223-239 (2006)). The mechanism by which immunogenicity is triggered remains unclear although the tolerance to self proteins may be broken by a number of factors linked to both the product and the subject (Chester et al., *Expert Rev. Clin. Immunol.* 1:549-559 (2006); Baker and Jones, *Curr. Opin. Drug Disc. Dev.* 10:219-227 (2007)). For the product, these include dose, frequency of administration, route, immunomodulatory capacity of the protein therapeutic, and the formulation (Jaber and Baker, *J. Pharm. Biomed. Anal.* 43:1256-1261 (2007)). For the subject, factors such as immune competence (i.e., whether the subject is receiving immunosuppressive treatment), subject's MHC haplotype and intrinsic tolerance to the protein therapeutic will influence immunogenicity. Regardless of how immunogenicity is triggered, one of the single most important factors in the development of an ensuing immune response is the presence of epitopes that are able to effectively stimulate a potent CD4+ T cell response (Baker and Jones, *Curr. Opin. Drug Disc. Dev.* 10:219-227 (2007)).

T cells or T-lymphocytes are a subset of white blood cells known as lymphocytes. (The abbreviation "T" in T cell is for "thymus" since this is the primary organ responsible for T cell maturation.) T cells play a central role in cell-mediated immunity. They can be distinguished from other types of lymphocytes (such as B cells and natural killer cells (NK cells)), by the presence of cell-surface proteins called T cell receptors (TCRs). Different types of T cells have also been identified; these can be distinguished based on the differing functions they serve (e.g., CD4+ T cells (a.k.a., $T_H$ or T helper cells), CD8+ cytotoxic T cells (CTLs), memory T cells, regulatory T cells ($T_{reg}$ cells), natural killer cells (NK cells), and gamma delta T cells (γδ T cells)).

$T_H$ cells are so named because they aid other white blood cells in immunologic processes including, inter alia, assisting the maturation of B cells into plasma and B memory cells, and activation of cytotoxic T cells and macrophages. $T_H$ cells are also known as CD4+ T cells because they express CD4 protein on the cell-surface. Once activated, CD4+ T cells divide rapidly and secrete chemokines that further assist in activating or regulating immune responses.

Experimental evidence suggests that HIV-infected patients given L-carnitine in combination with standard antiretroviral treatment have greater improvement in CD4+ counts when compared to control patients given antiretroviral agents with no supplementation (Gomez-Solis et al., *Pharmacology* 88:10-17 (2011)). Acetylcarnitine has also been reported to have immunomodulating activity (U.S. Pat. No. 4,415,588).

SUMMARY OF THE DISCLOSURE

Applicants have found that β-hydroxy-γ-aminophosphonates and β-amino-γ-aminophosphonates having Formula I or Formula II, or stereoisomers thereof, (see below; collectively referred to herein as "compounds of the disclosure") stimulate the production of T-lymphocytes in a subject. Thus, in one aspect, the present disclosure provides methods of using β-hydroxy-γ-aminophosphonates or β-amino-γ-aminophosphonates having Formula I or Formula II, or stereoisomers thereof, as immunomodulating agents.

Applicants have also found that compounds of the disclosure inhibit the effect of lipopolysaccharide (LPS), induce cell proliferation, induce phagocytosis, and reduce mycetoma development in a subject.

In another aspect, the present disclosure provides methods for treating immune disorders, allergic disorders, or inflammatory disorders, or combinations thereof, in a subject comprising administering to the subject a therapeutically effective amount of a β-hydroxy-γ-aminophosphonate or β-amino-γ-aminophosphonate having Formula I or Formula II, or a stereoisomer thereof.

In another aspect, the present disclosure provides methods for treating immune disorders, allergic disorders, or inflammatory disorders, or combinations thereof, in a subject comprising administering to the subject a pharmaceutical composition comprising a therapeutically effective amount of a β-hydroxy-γ-aminophosphonate or β-amino-γ-aminophosphonate having Formula I or Formula II, or a stereoisomer thereof, and one or more pharmaceutically acceptable carriers.

In another aspect, the present disclosure provides methods for treating immune disorders, allergic disorders, or inflammatory disorders, or combinations thereof, in a subject comprising administering to the subject a therapeutically effective amount of a β-hydroxy-γ-aminophosphonate having Formula I, or a stereoisomer thereof.

In another aspect, the present disclosure provides methods for treating immune disorders, allergic disorders, or inflammatory disorders, or combinations thereof, in a subject comprising administering to the subject a pharmaceutical composition comprising a therapeutically effective amount of a β-hydroxy-γ-aminophosphonate having Formula I, or a stereoisomer thereof, and one or more pharmaceutically acceptable carriers.

In another aspect, the present disclosure provides methods for treating immune disorders, allergic disorders, or inflammatory disorders, or combinations thereof, in a subject comprising administering to the subject a therapeutically effective amount of a β-hydroxy-γ-aminophosphonate or β-amino-γ-aminophosphonate having Formula I or Formula II, or a stereoisomer thereof, and one or more additional therapeutic agents, e.g., immunomodulating or anti-inflammatory agents.

Exemplary immune, allergic, and/or inflammatory disorders include arthritis, type 1 insulin-dependent diabetes mellitus, adult respiratory distress syndrome, inflammatory bowel disease, dermatitis, meningitis, thrombotic thrombocytopenic purpura, Sjogren's syndrome, encephalitis, uveitis, leukocyte adhesion deficiency, rheumatoid arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, tissue specific autoimmunity, degenerative autoimmunity delayed hypersensitivities, autoimmune complications of AIDS, atrophic gastritis, ankylosing spondylitis and Addison's disease.

Applicants have also found that compounds of the disclosure reduce the degree of fat accumulation in the liver, reduce the levels of alanine aminotransferase (ALT), aspartate aminotransferase (AST), and alkaline phosphatase (AP), and reduce the levels of glucose, cholesterol, and triglycerides in obese subjects. Thus, in another aspect, the present disclosure provides methods of using a β-hydroxy-γ-aminophosphonate or β-amino-γ-aminophosphonate having Formula I or Formula II, or a stereoisomer thereof, as hepatoprotecting agents.

In another aspect, the present disclosure provides methods for providing hepatoprotection in a subject comprising administering to the subject a pharmaceutical composition comprising a therapeutically effective amount of a γ-hydroxy-γ-aminophosphonate or β-amino-γ-aminophosphonate having Formula I or Formula II, or a stereoisomer thereof, and one or more pharmaceutically acceptable carriers.

In another aspect, the present disclosure provides methods for providing hepatoprotection in a subject comprising administering to the subject a therapeutically effective amount of a β-hydroxy-γ-aminophosphonate or β-amino-γ-aminophosphonate having Formula I or Formula II, or a stereoisomer thereof, and one or more additional therapeutic agents e.g., hepatoprotecting agents.

Other features and advantages of the disclosure will be apparent from the following detailed description, and from the claims. The disclosed materials, methods, and examples are for illustrative purposes only and are not intended to be limiting. Skilled artisans will appreciate that methods and materials similar or equivalent to those described herein can be used to practice the disclosure.

Unless otherwise defined, all technical and scientific terms used herein have the meaning commonly understood by one skilled in the art to which this disclosure belongs. In case of conflict, the present specification, including definitions, will control.

BRIEF DESCRIPTION OF DRAWINGS

FIG. 17 is a photograph showing the effect of (2R,3S)-(2-hydroxy-5-methyl-3-trimethylammonium-hexyl)-phosphonic acid dimethyl ester; iodide (5 and 50 mg/kg) on mycetoma induced in mice.

DETAILED DESCRIPTION OF THE DISCLOSURE

Definitions

Figure 1:
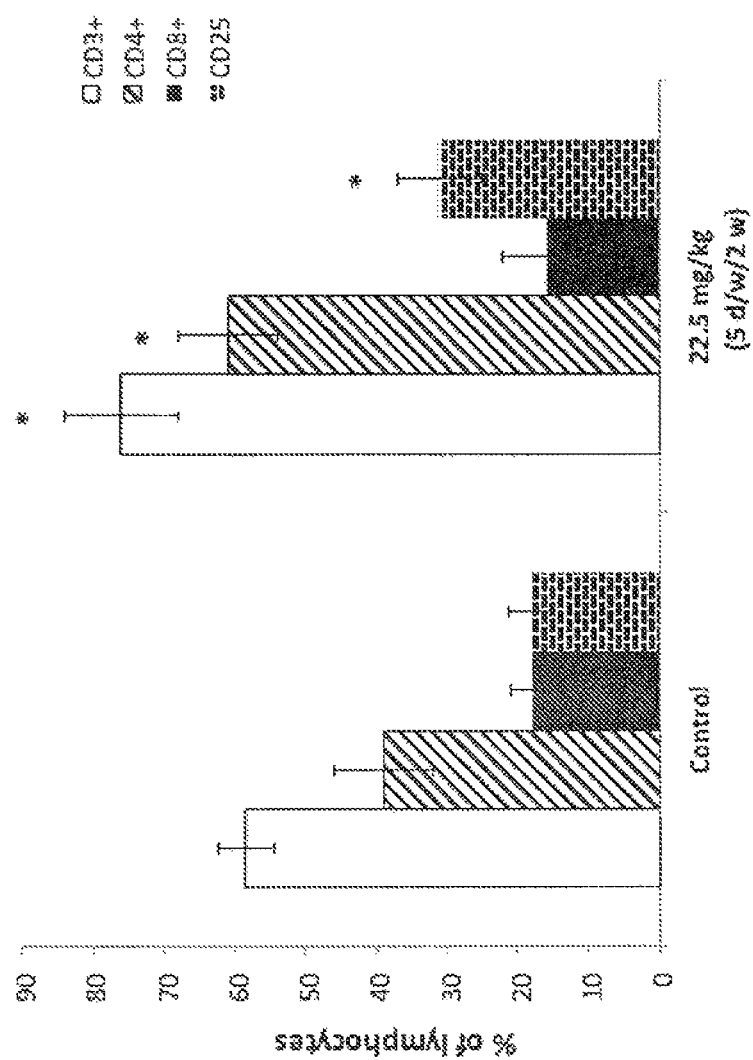
FIG. 1 is a bar graph showing the effect of (2R,3S)-(2-hydroxy-5-methyl-3-trimethylammonium-hexyl)-phosphonic acid; iodide (22.5 mg/kg) on lymphocyte levels in "normal" Wistar rats treated during two weeks. * p<0.01 compared to control group.

The term "alkyl" as used herein by itself or part of another group refers to a straight-chain or branched saturated aliphatic hydrocarbon having from one to eighteen carbons or the number of carbons designated, e.g., $C_1$-$C_{18}$ means from 1 to 18 carbons, inclusive. In one such embodiment, the alkyl is a $C_1$-$C_{10}$ alkyl. In another such embodiment, the alkyl is a $C_1$-$C_8$ alkyl. In another such embodiment, the alkyl is a $C_3$-$C_8$ alkyl. In certain such embodiments, the alkyl is a lower alkyl. Non-limiting exemplary alkyl groups according to certain aspects of the disclosure include methyl, ethyl, n-propyl, isopropyl, n-butyl, sec-butyl, isobutyl, tert-butyl, n-pentyl, isopentyl, n-hexyl, isohexyl, n-heptyl, 4,4-dimethylpentyl, n-octyl, 2,2,4-trimethylpentyl, nonyl, decyl, and the like.

The term "lower alkyl" as used herein by itself or part of another group means the alkyl as defined above has 1 to 6 carbons, i.e., a $C_1$-$C_6$-alkyl. Non-limiting exemplary lower alkyl groups include methyl, ethyl, n-propyl, isopropyl, n-butyl, sec-butyl, isobutyl, tert-butyl, n-pentyl, isopentyl, n-hexyl, and the like.

The term "optionally substituted alkyl" as used herein by itself or part of another group means that the alkyl as defined above is either unsubstituted or substituted with one, two or three substituents independently selected from hydroxy, i.e., —OH, nitro, i.e., —NO$_2$, cyano, i.e., —CN, halo, amino, optionally substituted cycloalkyl, optionally substituted heteroaryl, optionally substituted heterocyclo, alkoxy, aryloxy, aralkyloxy, alkylthio, carboxamido or sulfonamido. In one such embodiment, the optionally substituted alkyl is unsubstituted. In another such embodiment, the optionally substituted alkyl is substituted with one substituent. In another such embodiment, the optionally substituted alkyl is substituted with two substituents. In certain such embodiments, the substituents are selected from hydroxy, i.e., a hydroxyalkyl, halo, i.e., a haloalkyl, or amino, i.e., an aminoalkyl. In certain such embodiments, the optionally substituted alkyl is an optionally substituted $C_1$-$C_6$-alkyl, i.e., an optionally substituted lower alkyl. Exemplary optionally substituted alkyl groups include, but are not limited to, —CH$_2$OCH$_3$, —CH$_2$CH$_2$NH$_2$, —CH$_2$CH$_2$CN, —CH$_2$CONH$_2$, hydroxymethyl, hydroxyethyl, hydroxypropyl, trifluoromethyl, and the like.

The term "aralkyl" as used herein by itself or part of another group refers to an optionally substituted alkyl as defined above having one, two or three optionally substituted aryl substituents. In one such embodiment, the optionally substituted alkyl is unsubstituted. In another such embodiment, the optionally substituted aryl is unsubstituted. In certain such embodiments, the optionally substituted aryl is phenyl (abbreviated as "Ph"). In another such embodiment, the aralkyl has one optionally substituted aryl substituent. In another such embodiment, the aralkyl has two optionally substituted aryl substituents. In a particular embodiment, the aralkyl is an aryl($C_1$-$C_4$ alkyl). In certain such embodiments, the aryl($C_1$-$C_4$ alkyl) has one optionally substituted aryl substituent. Non-limiting exemplary aralkyl groups include, for example, benzyl, phenylethyl, (4-fluorophenyl)ethyl, phenylpropyl, diphenylmethyl (i.e., $Ph_2CH$—), diphenylethyl (i.e., $Ph_2CHCH_2$—), and the like.

The term "cycloalkyl" as used herein by itself or part of another group refers to saturated and partially unsaturated (containing one or two double bonds) cyclic hydrocarbon groups containing one to three rings having from three to twelve carbon atoms (i.e., $C_3$-$C_{12}$ cycloalkyl) or the number of carbons designated. In one such embodiment, the cycloalkyl has one ring. In another such embodiment, the cycloalkyl is a $C_3$-$C_7$ cycloalkyl. Non-limiting exemplary cycloalkyl groups include cyclopropyl, cyclobutyl, cyclopentyl, cyclohexyl, cycloheptyl, cyclooctyl, norbornyl, decalin, adamantyl, and the like.

The term "optionally substituted cycloalkyl" as used herein by itself or part of another group means the cycloalkyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. The term "optionally substituted cycloalkyl" also means the cycloalkyl as defined above may be fused to an optionally substituted aryl.

The term "alkenyl" as used herein by itself or part of another group refers to an alkyl group as defined above containing one, two or three carbon-to-carbon double bonds. In one embodiment, the alkenyl has one carbon-to-carbon double bond. Non-limiting exemplary alkenyl groups include —CH=$CH_2$, —$CH_2$CH=$CH_2$, —$CH_2CH_2$CH=$CH_2$, —$CH_2CH_2$CH=$CHCH_3$ and the like. Other suitable alkenyl groups will be familiar to those of ordinary skill in the relevant arts.

The term "optionally substituted alkenyl" as used herein by itself or part of another group means the alkenyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Non-limiting exemplary optionally substituted alkenyl groups include —CH=CH—, —CH=CHPh, —$CH_2$CH=CHPh, and the like.

The term "alkynyl" as used herein by itself or part of another group refers to an alkyl group as defined above containing one to three carbon-to-carbon triple bonds. In one embodiment, the alkynyl has one carbon-to-carbon triple bond. Non-limiting exemplary alkynyl groups include —C≡CH, —C≡$CCH_3$, —$CH_2$C≡CH, —$CH_2CH_2$C≡CH and —$CH_2CH_2$C≡$CCH_3$.

The term "optionally substituted alkynyl" as used herein by itself or part of another group means the alkynyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Non-limiting exemplary optionally substituted alkenyl groups include —C≡CPh, —$CH_2$C≡CPh and the like.

The term "aryl" as used herein by itself or part of another group refers to monocyclic and bicyclic aromatic ring systems having from six to fourteen carbon atoms (i.e., $C_6$-$C_{14}$ aryl) such as phenyl (abbreviated as Ph), 1-naphthyl and 2-naphthyl, and the like.

The term "optionally substituted aryl" as used herein by itself or part of another group means the aryl as defined above is either unsubstituted or substituted with one to five substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. In one such embodiment, the optionally substituted aryl is an optionally substituted phenyl, which in certain embodiments has four substituents, three substituents, two substituents or one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl and 3,5-dimethoxy, 4-methylphenyl and the like. As used herein, the term "optionally substituted aryl" is also meant to include groups having fused optionally substituted cycloalkyl and fused optionally substituted heterocyclo rings.

The term "heteroaryl" as used herein by itself or part of another group refers to monocyclic and bicyclic aromatic ring systems typically having from five to fourteen carbon atoms (i.e., $C_5$-$C_{14}$ heteroaryl) and one, two, three or four heteroatoms independently selected from the group consisting of oxygen, nitrogen and sulfur. In one such embodiment, the heteroaryl has four heteroatoms. In another such embodiment, the heteroaryl has three heteroatoms. In another such embodiment, the heteroaryl has two heteroatoms. In another such embodiment, the heteroaryl has one heteroatom. Non-limiting exemplary heteroaryl groups include 1-pyrrolyl, 2-pyrrolyl, 3-pyrrolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, purinyl, 2-benzimidazolyl, 4-benzimidazolyl, 5-benzimidazolyl, 2-benzthiazolyl, 4-benzthiazolyl, 5-benzthiazolyl, 5-indolyl, 3-indazolyl, 4-indazolyl, 5-indazolyl, 1-isoquinolyl, 5-isoquinolyl, 2-quinoxalinyl, 5-quinoxalinyl, 2-quinolyl, 3-quinolyl, 6-quinolyl and the like. As used herein, the term "heteroaryl" is also meant to include possible N-oxides. Non-limiting exemplary N-oxides include pyridyl N-oxide and the like.

The term "optionally substituted heteroaryl" as used herein by itself or part of another group means the heteroaryl as defined above is either unsubstituted or substituted with one to four substituents, typically one or two substituents, which are typically independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. In one such embodiment, the optionally substituted heteroaryl has one substituent. According to this aspect of the disclosure, any available carbon or nitrogen atom may be substituted.

The term "heterocyclo" as used herein by itself or part of another group refers to saturated and partially unsaturated (containing one or two double bonds) cyclic groups containing one to three rings having from two to twelve carbon atoms (i.e., $C_2$-$C_{12}$ heterocyclo) and one or two oxygen, sulfur or nitrogen atoms.

The term "optionally substituted heterocyclo" as used herein by itself or part of another group means the heterocyclo as defined above is either unsubstituted or substituted with one to four substituents which are typically independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Substitution may occur on any available carbon or nitrogen atom.

The term "alkoxy" as used herein by itself or part of another group refers to a haloalkyl, optionally substituted alkyl, optionally substituted cycloalkyl, optionally substituted alkenyl or optionally substituted alkynyl attached to a terminal oxygen atom. Non-limiting exemplary alkoxy groups include methoxy, tert-butoxy, —OCH$_2$CH=CH$_2$ and the like.

The term "aryloxy" as used herein by itself or part of another group refers to an optionally substituted aryl attached to a terminal oxygen atom. Non-limiting exemplary aryloxy groups include phenoxy and the like.

The term "aralkyloxy" as used herein by itself or part of another group refers to an aralkyl attached to a terminal oxygen atom. Non-limiting exemplary aralkyloxy groups include benzyloxy and the like.

The term "alkylthio" as used herein by itself or part of another group refers to a haloalkyl, aralkyl, optionally substituted alkyl, optionally substituted cycloalkyl, optionally substituted alkenyl or optionally substituted alkynyl attached to a terminal sulfur atom. Non-limiting exemplary alkyl groups include —SCH$_3$ and the like.

The term "halo" or "halogen" as used herein by itself or part of another group refers to fluoro, chloro, bromo or iodo. In certain embodiments of the present disclosure, the halo is fluoro or chloro.

The term "amino" as used herein by itself or part of another group refers to a radical of formula —NR$^a$R$^b$ wherein R$^a$ and R$^b$ are independently hydrogen, haloalkyl, aralkyl, optionally substituted alkyl, optionally substituted cycloalkyl, optionally substituted heterocyclo, optionally substituted aryl or optionally substituted heteroaryl; or R$^a$ and R$^b$ taken together with the nitrogen atom to which they are attached form a four to seven membered optionally substituted heterocyclo. Non-limiting exemplary amino groups include —NH$_2$, —N(H)CH$_3$, —N(CH$_3$)$_2$, N(H)CH$_2$CH$_3$, N(CH$_2$CH$_3$), —N(H)CH$_2$Ph and the like.

The term "carboxamido" as used herein by itself or part of another group refers to a radical of formula —CO-amino. Non-limiting exemplary carboxamido groups include —CONH$_2$, —CON(H)CH$_3$, —CON(H)Ph, —CON(H)CH$_2$CH$_2$Ph, —CON(CH$_3$)$_2$, CON(H)CHPh$_2$ and the like.

The term "sulfonamido" as used herein by itself or part of another group refers to a radical of formula —SO$_2$-amino. Non-limiting exemplary sulfonamido groups include —SO$_2$NH$_{12}$, —SO$_2$N(H)CH, —SO$_2$N(H)Ph and the like.

The term "about," as used herein, includes the recited number±10%. Thus, "about 10" means 9 to 11, inclusive.

The term "$C_1$-$C_4$ alcohol" as used herein refers to an alcohol having 1 to 4 carbons such as methanol, ethanol, propanol, isopropanol, butanol, isobutanol, sec-butanol and tert-butanol. In one embodiment, the $C_1$-$C_4$ alcohol is methanol.

The term "monovalent pharmaceutically acceptable cation" as used herein refers to inorganic cations such as, but not limited to, alkaline metal ions, e.g., Na$^+$ and K$^+$, as well as organic cations such as, but not limited to, ammonium and substituted ammonium ions, e.g., NH$_4^+$, NHMe$_3^+$, NH$_2$HMe$_2^+$, NHTMe$_3^+$ and NMe$_4^+$.

The term "divalent pharmaceutically acceptable cation" as used herein refers to inorganic cations such as, but not limited to, alkaline earth metal cations, e.g., Ca$^{2+}$ and Mg$^{2+}$.

Examples of monvalent and divalent pharmaceutically acceptable cations are discussed in Berge et al. *J. Pharm. Sci.*, 66, 1997, 1-19, the disclosure of which is incorporated herein by reference.

The term "pharmaceutically acceptable anion" as used herein refers to an anion associated with a quaternary ammonium compound of the present disclosure that is acceptable for administration to a subject, e.g., a mammal, e.g., a human. In one embodiment, the pharmaceutically acceptable anion is the anion of a pharmaceutically acceptable inorganic acid, e.g., hydrochloric, perchloric, sulfuric, phosphoric, hydrobromic, hydroiodic or nitric acid and the like. In one embodiment, the pharmaceutically acceptable anion is the anion of a pharmaceutically acceptable organic acid, e.g., a mono or polyvalent organic acid, e.g., citric, fumaric, maleic, malic, ascorbic, succinic, tartaric, benzoic, acetic, phenylacetic, methanesulfonic, ethansulfonic, benzenesulfonic or p-toluenesulfonic acid and the like.

The term "pharmaceutically acceptable salt," as used herein, refers to any salt (e.g., obtained by reaction with an acid or a base) of a compound of the present disclosure that is physiologically tolerated in the target animal (e.g., a mammal, such as a human). Salts of the compounds of the present disclosure may be derived from inorganic or organic acids and bases. Examples of suitable acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, boronic, malonic, sulfonic, picolinic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the disclosure and their pharmaceutically acceptable acid addition salts.

Examples of suitable bases include, but are not limited to, alkali metal (e.g., sodium) hydroxides, alkaline earth metal (e.g., magnesium) hydroxides, ammonia, and compounds of formula NW$_4^+$, wherein W is $C_{1-4}$ alkyl, and the like.

Examples of suitable such salts include, but are not limited to: acetate, adipate, alginate, aspartate, benzoate, benzenesulfonate, bisulfate, borate, boronate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, nitrate, sulfate, picolinate, besylate, perchloriate, salicylate, phosphate, and the like. Other examples of suitable salts according to the disclosure include anions of the compounds of the present disclosure compounded with a suitable cation such as $Na^+$, $K^+$, $Ca^{2+}$, $Mg^{2+}$, $Mn^{2+}$, $NH_4^+$, and $NW_4^+$ (wherein W is a $C_{1-4}$ alkyl group), and the like, including additional pharmaceutically acceptable salts that are well known in the art (see, e.g., Remington's Pharmaceutical Sciences, Mack Publishing Co., Easton, Pa., 19th ed. 1995) and others that are known to those of ordinary skill in the relevant arts. For therapeutic use, salts of the compounds of the present disclosure are contemplated as being pharmaceutically acceptable. However, salts of acids and bases that are non-pharmaceutically acceptable may also find use, for example, in the preparation or purification of a pharmaceutically acceptable compound.

The term "pharmaceutical composition" as used herein refers to a composition comprising one or more active pharmaceutical ingredients including, but not limited to, one or more compounds of the disclosure which can be used to treat, prevent or reduce the severity of a disease, disorder or condition in a subject, e.g., a mammal such as a human, that is suffering from, that is predisposed to, or that has been exposed to the disease, disorder or condition. A pharmaceutical composition generally comprises an effective amount of one or more active agents, e.g., a compound having Formula I or Formula II, or a stereoisomer thereof, and one of more pharmaceutically acceptable carriers. The pharmaceutical composition can also a comprise a compound of the disclosure and one or more additional ingredients, including but not limited to one or more therapeutic agents such as one or more immunomodulating agents, or one or more anti-inflammatory agents, or one or more anti-allergic agents.

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences, Mack Publishing Co., Easton, Pa., 19th ed. 1995. Preferred pharmaceutical carriers depend upon the intended mode of administration of the active agent. Typical modes of administration are described below.

The term "therapeutically effective amount," as used herein, refers to that amount of a given therapeutic agent sufficient to result in amelioration of one or more symptoms of a disorder or condition, or prevent appearance or advancement of a disorder or condition, or cause regression of or cure from the disorder or condition.

The term "therapeutic agent," as used herein refers to any chemical substance that can be used in the treatment, management, prevention or amelioration of a disease, condition or disorder or one or more symptoms thereof. Suitable therapeutic agents include, but are not limited to, small molecules, synthetic drugs, peptides, polypeptides, proteins, nucleic acids (e.g., DNA and RNA polynucleotides including, but not limited to, antisense nucleotide sequences, triple helices, and nucleotide sequences encoding biologically active proteins, polypeptides, or peptides), antibodies, synthetic or natural inorganic molecules, mimetic agents, and synthetic or natural organic molecules. In some embodiments, the therapeutic agent is one which is known to be useful for, or has been or is currently being used for, the treatment, management, prevention or amelioration of a condition or disorder or one or more symptoms thereof. In one embodiment, the therapeutic agent is an immunomodulating agent, e.g., azathioprine, 6-mercaptopurine, cyclosporine A, tacrolimus, and methotrexate.

The stereochemical terms and conventions used in the specification are consistent with those described in Pure & Appl. Chem. 68:2193 (1996), unless otherwise indicated.

The term "purity," as used herein, refers to chemical and/or stereoisomeric (i.e., diastereomeric or enantiomeric) purity, unless otherwise indicated.

The term "substantially free," as used herein, refers to a composition comprising at least about 90% by weight of one stereoisomer, i.e., enantiomer or diastereomer, over all of the other possible stereoisomers. In another embodiment, the composition comprises at least about 91%, about 92%, about 93%, about 94%, about 95%, about 96%, about 97%, about 98%, about 99% or about 99.5% by weight of the desired stereoisomer.

Throughout the specification, groups and optional substituents thereof are chosen to provide stable moieties and compounds.

Compounds of the present disclosure exist as stereoisomers including optical isomers. The disclosure includes all stereoisomers, as pure individual stereoisomer preparations and as enriched preparations of each, and as the racemic mixtures of such stereoisomers as well as the individual enantiomers and diastereomers that may be separated according to methods that are well-known to those of skill in the art.

Overview

The present disclosure provides β-hydroxy-γ-aminophosphonates and β-amino-γ-aminophosphonates, or stereoisomers thereof, that, inter alia, stimulate the production of T-lymphocytes in a subject. As immunostimulating agents, the β-hydroxy-γ-aminophosphonates and β-amino-γ-aminophosphonates of the present disclosure are useful for treating various diseases, conditions, and disorders including immune disorders, allergic disorders, and inflammatory disorders, or combinations thereof.

In one embodiment, the present disclosure provides β-hydroxy-γ-aminophosphonates and β-amino-γ-aminophosphonates having of Formula I:

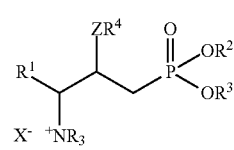

wherein:
each R is independently selected from the group consisting of hydrogen and lower alkyl;
$R^1$ is selected from the group consisting of, optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

$R^2$ and $R^3$ are independently selected from the group consisting of hydrogen, optionally substituted alkyl, aralkyl, optionally substituted aryl, and monovalent pharmaceutically acceptable cation, or taken together $R^2$ and $R^3$ represent a divalent pharmaceutically acceptable cation;

$R^4$ is selected from the group consisting of hydrogen, optionally substituted alkyl, optionally substituted cycloalkyl, optionally substituted alkenyl, optionally substituted alkynyl, and $COR^5$;

$R^5$ is selected from the group consisting of optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

$X^-$ is a pharmaceutically acceptable anion, or $X^-$ and $R^2$ are absent and the compound of Formula I is a zwitterion, Z is selected from the group consisting of O and $NR^{10}$; and $R^{10}$ is selected from the group consisting of hydrogen, optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

or pharmaceutically acceptable hydrates, crystalline forms or amorphous forms thereof, or a stereoisomer thereof, for use in methods of the present disclosure, e.g., in methods of stimulating the production of T-lymphocytes in a subject, and/or in methods of treating diseases, conditions, or disorders in a subject, and/or in methods of providing hepatoprotection in a subject.

In another embodiment, a compound of Formula I is a mixture of stereoisomers, e.g., a mixture of diastereomers and/or enantiomers. In another embodiment, a compound of Formula I is a mixture of diastereomers. In another embodiment, a compound of Formula I is a mixture of enantiomers. In another embodiment, a compound of Formula I is a single enantiomer.

In another embodiment, the compound having Formula I is a stereoisomer, or a mixture of stereoisomers, i.e., a compound having Formula 3S-I; 3R-I; 2R,3S-I; 2S,3S-I; 2R,3R-I; or 2S,3R-I:

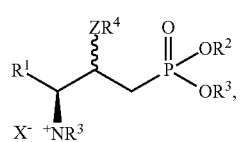

3S-I

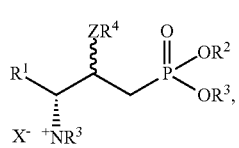

3R-I

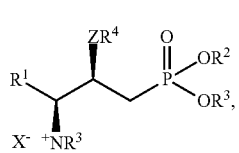

2R,3S-I

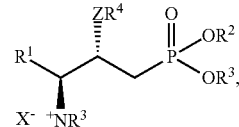

2S,3S-I

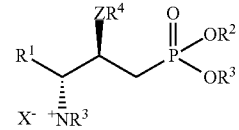

2R,3R-I or

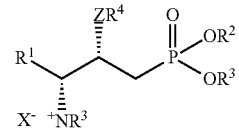

2S,3R-I or pharmaceutically acceptable hydrates, crystalline forms or amorphous forms of any one thereof, wherein R, $R^1$, $R^2$, $R^3$, $R^4$, $X^-$ and Z have the meanings as described above for Formula I, or pharmaceutically acceptable hydrates, crystalline forms or amorphous forms thereof.

In another embodiment, the compound having Formula I is a compound having Formula 2R,3S-I, i.e., the 2R,3S-isomer of Formula I, or pharmaceutically acceptable hydrates, crystalline forms or amorphous forms thereof. In another embodiment, the compound having Formula 2R,3S-I is substantially tree from all other Formula I isomers.

In another embodiment, the compound having Formula I, or stereoisomer thereof, is a compound wherein:

each R is independently lower alkyl;

$R^1$ is selected from the group consisting of n-propyl, isopropyl, n-butyl, isobutyl, sec-butyl, tert-butyl, aralkyl, optionally substituted cycloalkyl, optionally substituted alkenyl, optionally substituted alkynyl, optionally substituted aryl, optionally substituted heteroaryl, and optionally substituted heterocyclo;

$R^2$ and $R^3$ are independently selected from the group consisting of hydrogen. optionally substituted alkyl, aralkyl, optionally substituted aryl, and monovalent pharmaceutically acceptable cation, or taken together $R^2$ and $R^3$ represent a divalent pharmaceutically acceptable cation;

$R^4$ is selected from the group consisting of hydrogen, optionally substituted alkyl, optionally substituted cycloalkyl, optionally substituted alkenyl, optionally substituted alkynyl, and $COR^5$;

$R^5$ is selected from the group consisting of optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

$X^-$ is a pharmaceutically acceptable anion, or $X^-$ and $R^2$ are absent and the compound of Formula I is a zwitterion;

Z is selected from the group consisting of O and $NR^{10}$; and $R^{10}$ is selected from the group consisting of hydrogen, optionally substituted alkyl, aralkyl, optionally substituted cycloalkyl, optionally substituted alkenyl, optionally substituted alkynyl, optionally substituted aryl, optionally substituted heteroaryl, and optionally substituted heterocyclo;

or pharmaceutically acceptable hydrates, crystalline forms or amorphous forms thereof, or stereoisomers thereof.

In another embodiment, the compound having Formula I, or stereoisomer thereof, is a compound wherein each R is methyl, or pharmaceutically acceptable hydrates, crystalline forms or amorphous forms thereof.

In another embodiment, the compound having Formula I, or stereoisomer thereof, is a compound wherein $R^1$ is isobutyl, or pharmaceutically acceptable hydrates, crystalline forms or amorphous forms thereof.

In another embodiment, the compound having Formula I, or stereoisomer thereof, is a compound wherein Z is O, or pharmaceutically acceptable hydrates, crystalline forms or amorphous forms thereof.

In another embodiment, the compound having Formula I, or stereoisomer thereof, is a compound wherein $R^4$ is hydrogen, or pharmaceutically acceptable hydrates, crystalline forms or amorphous forms thereof.

In another embodiment, the compound having Formula I, or stereoisomer thereof, is a compound wherein $R^4$ is —COCH$_3$, or pharmaceutically acceptable hydrates, crystalline forms or amorphous forms thereof.

In another embodiment, the compound having Formula I, or stereoisomer thereof, is a compound wherein $R^2$ and $R^3$ are independently selected from the group consisting of hydrogen and $C_1$-$C_3$ alkyl, or pharmaceutically acceptable hydrates, crystalline forms or amorphous forms thereof.

In another embodiment, the compound having Formula I, or stereoisomer thereof, is a compound wherein $R^2$ and $R^3$ are hydrogen, or pharmaceutically acceptable hydrates, crystalline forms or amorphous forms thereof.

In another embodiment, the compound having Formula I, or stereoisomer thereof, is a compound wherein $R^2$ and $R^3$ are methyl, or pharmaceutically acceptable hydrates, crystalline forms or amorphous forms thereof.

In another embodiment, the compound having Formula I, or stereoisomer thereof, is a compound wherein $X^-$ is selected from the group consisting of hydroxide, chloride, bromide, iodide, sulphate, nitrate, phosphate, formate, acetate, maleate, fumarate, citrate, oxalate, succinate, tartrate, malate, mandelate, lactate, gluconate, trifluoroacetate, methanesulphonate, besylate and p-toluenesulphonate, or pharmaceutically acceptable hydrates, crystalline forms or amorphous forms thereof.

In another embodiment, the compound having Formula I, or stereoisomer thereof, is a compound wherein $R^1$ is selected from the group consisting of n-propyl, isopropyl, n-butyl, isobutyl, sec-butyl, tert-butyl, benzyl, and phenyl, $R^2$ and $R^3$ are independently selected from the group consisting hydrogen, methyl, ethyl, n-propyl, isopropyl, n-butyl, isobutyl, sec-butyl, tert-butyl, isopenyl, benzyl, and phenyl, and $R^4$ and $R^{10}$ are hydrogen, or pharmaceutically acceptable hydrates, crystalline forms or amorphous forms thereof.

In another embodiment, the present disclosure provides zwitterionic compounds having Formula II:

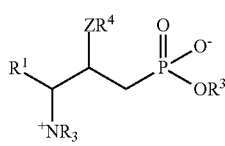

II or pharmaceutically acceptable hydrates, crystalline forms or amorphous forms thereof, particularly wherein R, $R^1$, $R^3$, $R^4$ and Z have the meanings as described above for Formula I, for use in methods of the present disclosure, e.g., in methods of stimulating the production of T lymphocytes in a subject, and/or in methods of treating diseases, conditions, or disorders in a subject.

In another embodiment, the compound of Formula II is a mixture of stereoisomers, e.g., a mixture of diastereomers and/or enantiomers. Thus, in one particular such embodiment, a compound of Formula II is a mixture of diastereomers. In another particular such embodiment, a compound of Formula I is a mixture of enantiomers. In yet another embodiment, a compound of Formula II is a single enantiomer.

In another embodiment, the zwitterionic compounds having Formula II is a stereoisomer, or mixture of stereoisomers, i.e., a compound having Formula 3S-II; 3R-11; 2R,3S-II; 2S,3S-I; 3R,3R-II; or 2S,3R-II:

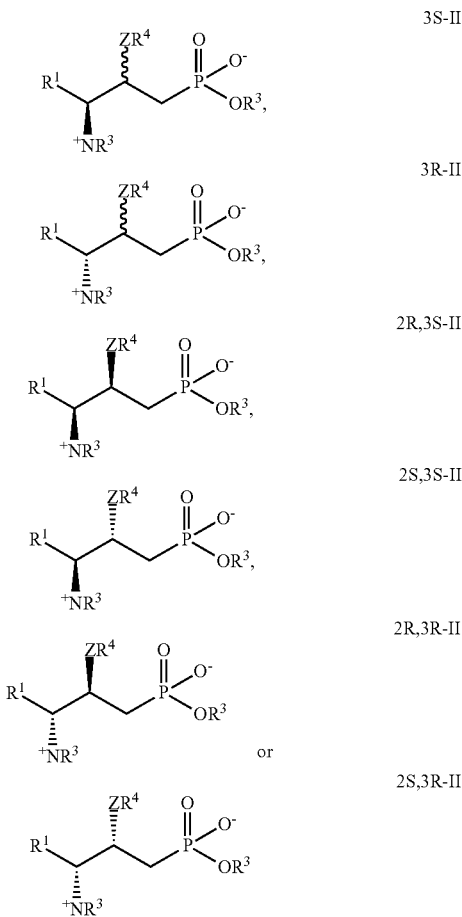

or pharmaceutically acceptable hydrates, crystalline forms or amorphous forms of any one thereof, wherein R, $R^1$, $R^3$, $R^4$ and Z have the meanings as described above for Formula I, or pharmaceutically acceptable hydrates, crystalline forms or amorphous forms thereof.

In another embodiment, the compound having Formula I is selected from the group consisting of:

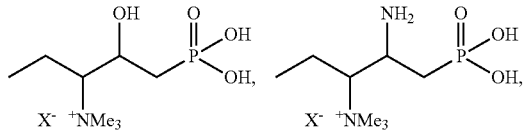

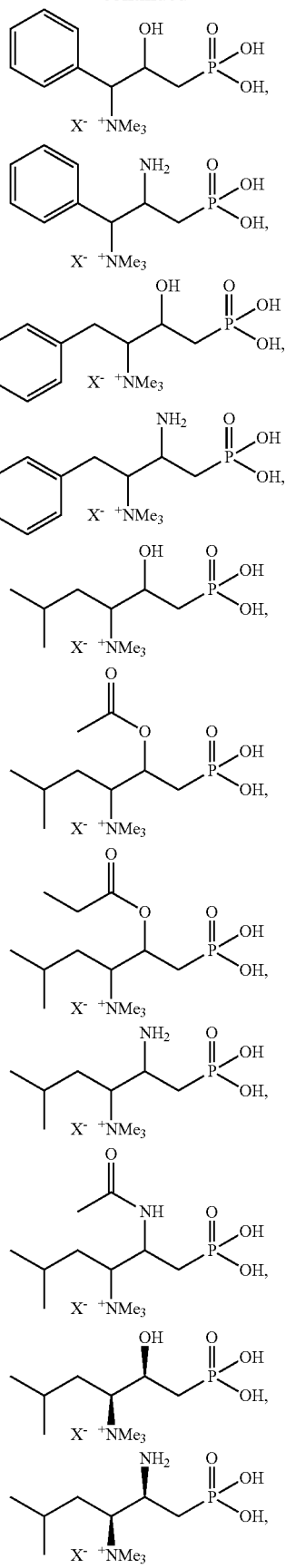
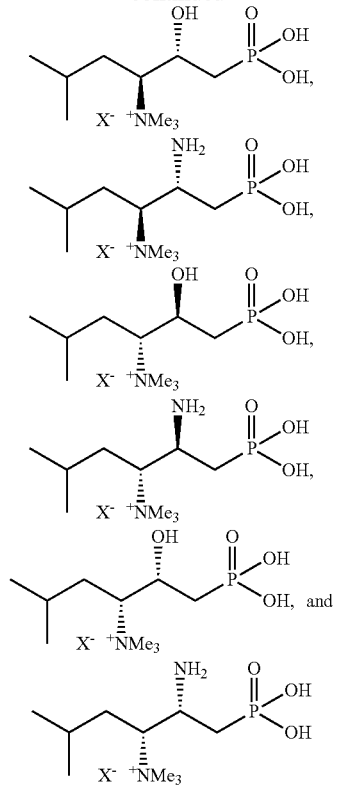
wherein X is a pharmaceutically acceptable anion, e.g., Cl⁻, I⁻, or Br⁻, or pharmaceutically acceptable hydrates, crystalline forms or amorphous forms thereof.
In another embodiment, the compound having Formula I is selected from the group consisting of:
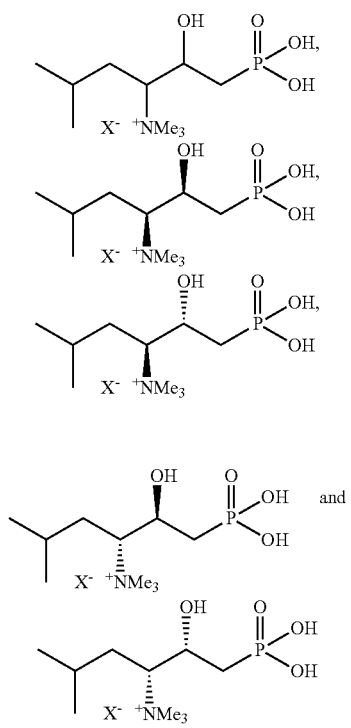

wherein X is a pharmaceutically acceptable anion, e.g., Cl⁻, I⁻, or Br⁻, or pharmaceutically acceptable hydrates, crystalline forms or amorphous forms thereof.

In another embodiment, the compound having Formula I is selected from the group consisting of:

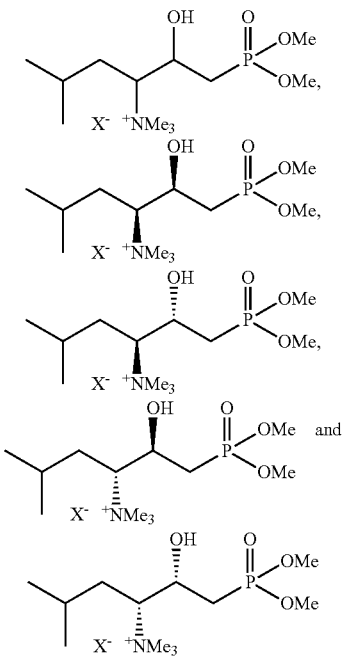

wherein X is a pharmaceutically acceptable anion, e.g., Cl⁻, I⁻, or Br⁻, or pharmaceutically acceptable hydrates, crystalline forms or amorphous forms thereof.

In another embodiment, the compound having Formula I is a compound selected from the group consisting of:

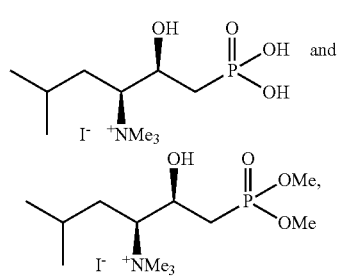

or pharmaceutically acceptable hydrates, crystalline forms or amorphous forms thereof.

In another embodiment, the compound having Formula I is:

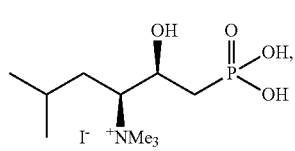

i.e., (2R,3S)-(2-hydroxy-5-methyl-3-trimethylammonium-hexyl)-phosphonic acid; iodide, or pharmaceutically acceptable hydrates, crystalline forms or amorphous forms thereof.

In another embodiment, the compound having Formula I is:

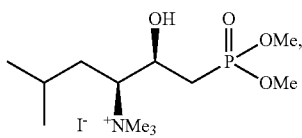

i.e., (2R,3S)-(2-hydroxy-5-methyl-3-trimethylammonium-hexyl)-phosphonic acid dimethyl ester; iodide, or pharmaceutically acceptable hydrates, crystalline forms or amorphous forms thereof.

The β-hydroxy-γ-aminophosphonates and β-amino-γ-aminophosphonates of the present disclosure having Formula I or Formula II, or pharmaceutically acceptable hydrates, crystalline forms or amorphous forms thereof, or stereoisomers thereof, are prepared as described in U.S. Pat. No. 8,178,515.

In another embodiment, the present disclosure provides methods of modulating the number of T-lymphocytes in the blood of a subject comprising administering to the subject β-hydroxy-γ-aminophosphonates or β-amino-γ-aminophosphonates having Formula I or Formula II, or stereoisomers thereof, or pharmaceutical compositions thereof.

In another embodiment, the present disclosure provides methods of stimulating the production of T-lymphocytes in a subject, comprising administering to the subject β-hydroxy-γ-aminophosphonates or β-amino-γ-aminophosphonates having Formula I or Formula II, or stereoisomers thereof, or pharmaceutical compositions thereof.

In another embodiment, the present disclosure provides methods of increasing the level of T-lymphocytes in a subject, comprising administering to the subject β-hydroxy-γ-aminophosphonates or β-amino-γ-aminophosphonates having Formula I or Formula II, or stereoisomers thereof, or pharmaceutical compositions thereof.

In another embodiment, administration of β-hydroxy-γ-aminophosphonates or β-amino-γ-aminophosphonates having Formula I or Formula II, or pharmaceutically acceptable hydrates, crystalline forms or amorphous forms thereof, or pharmaceutical compositions thereof, to a subject increases the level of total T-lymphocytes in the subject by about 2% to about 100%, e.g., by about 5% to about 50%, e.g., by about 10% to about 40%. In another embodiment, administration of β-hydroxy-γ-aminophosphonates or β-amino-γ-aminophosphonates having Formula I or Formula II, or pharmaceutically acceptable hydrates, crystalline forms or amorphous forms thereof, or pharmaceutical compositions thereof, to a subject increases the level of total T-lymphocytes in the subject by about 5%, about 10%, about 15%, about 20%, about 25%, about 30%, about 35%, about 40%, about 45%, about 50%, about 55%, about 60%, about 65%, about 70%, or about 75%, or more. The level of T-lymphocytes in a subject can be determined using methods well known by those skilled in the art such as flow cytometry.

In another embodiment, administration of β-hydroxy-γ-aminophosphonates or β-amino-γ-aminophosphonates having Formula I or Formula II, or pharmaceutically acceptable hydrates, crystalline forms or amorphous forms thereof, or pharmaceutical compositions thereof, to a subject increases the level of T helper cells in the subject by about 2% to about 100%, e.g., by about 5% to about 50%, e.g., by about 10% to about 40%. In another embodiment, administration of β-hydroxy-γ-aminophosphonates or β-amino-γ-aminophosphonates having Formula I or Formula II, or pharmaceutically acceptable hydrates, crystalline forms or amorphous forms thereof, or pharmaceutical compositions thereof, to a subject increases the level of T helper cells in the subject by about 5%, about 10%, about 15%, about 20%, about 25%, about 30%, about 35%, about 40%, about 45%, about 50%, about 55%, about 60%, about 65%, about 70%, or about 75%, or more.

In another embodiment, administration of β-hydroxy-γ-aminophosphonates and β-amino-γ-aminophosphonates having Formula I or Formula II, or pharmaceutically acceptable hydrates, crystalline forms or amorphous forms thereof, or pharmaceutical compositions thereof, to a subject increases the level of $T_{reg}$ cells in the subject by about 2% to about 100%, e.g., by about 5% to about 50%, e.g., by about 10% to about 40%. In another embodiment, administration of β-hydroxy-γ-aminophosphonates or β-amino-γ-aminophosphonates having Formula I or Formula II, or pharmaceutically acceptable hydrates, crystalline forms or amorphous forms thereof, or pharmaceutical compositions thereof, to a subject increases the level of $T_{reg}$ cells in the subject by about 5%, about 10%, about 15%, about 20%, about 25%, about 30%, about 35%, about 40%, about 45%, about 50%, about 55%, about 60%, about 65%, about 70%, or about 75%, or more.

In another embodiment, administration of β-hydroxy-γ-aminophosphonates and β-amino-γ-aminophosphonates having Formula I or Formula II, or pharmaceutically acceptable hydrates, crystalline forms or amorphous forms thereof, or pharmaceutical compositions thereof, to a subject increases the level of cytotoxic T cells in the subject by about 5% to about 100%, e.g. by about 5% to about 50%, e.g., by about 10% to about 40%. In another embodiment, administration of β-hydroxy-γ-aminophosphonates and β-amino-γ-aminophosphonates having Formula I or Formula II, or pharmaceutically acceptable hydrates, crystalline forms or amorphous forms thereof, or pharmaceutical compositions thereof, to a subject increases the level of cytotoxic T cells in the subject by about 5%, about 10%, about 15%, about 20%, about 25%, about 30%, about 35%, about 40%, about 45%, about 50%, about 55%, about 60%, about 65%, about 70%, or about 75%, or more.

In another embodiment, β-hydroxy-γ-aminophosphonates or β-amino-γ-aminophosphonates having Formula I or Formula II, or a stereoisomers thereof, or pharmaceutical compositions thereof, are used to treat immune disorders in a subject. As used herein, the term "immune disorder" refers to a disease, disorder, or condition caused by the immune system of a subject, e.g., an animal, e.g., a human, including autoimmune disorders. Immune disorders include those diseases, disorders, or conditions that have an immune component, and those that are substantially or entirely immune system-mediated. Autoimmune disorders are those wherein the subjects own immune system mistakenly attacks itself, thereby targeting the cells, tissues, and/or organs of the subjects own body. For example, the autoimmune reaction is directed against the nervous system in multiple sclerosis and the gut in Crohn's disease, in other autoimmune disorders such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus. Specific autoimmune disorders that may be ameliorated using the compounds and methods of this disclosure include without limitation, autoimmune disorders of the nervous system (e.g., multiple sclerosis, myasthenia gravis, autoimmune neuropathies such as Guillain-Barre, and autoimmune uveitis), autoimmune disorders of the blood (e.g., autoimmune hemolytic anemia, pernicious anemia, and autoimmune thrombocytopenia), autoimmune disorders of the blood vessels (e.g., temporal arteritis, anti-phospholipid syndrome, vasculitides such as Wegener's granulomatosis, and Behcet's disease), autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease, Hashimoto's thyroiditis, autoimmune oophoritis and orchitis, and autoimmune disorder of the adrenal gland); and autoimmune disorders of multiple organs (including connective tissue and musculoskeletal system diseases) (e.g., rheumatoid arthritis, systemic lupus erythematosus, scleroderma, polymyositis, dennatomyositis, spondyloarthropathies such as ankylosing spondylitis, and Sjogren's syndrome). In addition, other immune system mediated diseases, such as graft-versus-host disease and allergic disorders, are also included in the definition of immune disorders herein. Because a number of immune disorders are caused by inflammation, there is some overlap between disorders that are considered immune disorders and inflammatory disorders. For the purpose of this disclosure, in the case of such an overlapping disorder, it may be considered either an immune disorder or an inflammatory disorder.

"Treating an immune disorder" as used herein refers to administering a β-hydroxy-γ-aminophosphonate or β-amino-γ-aminophosphonate having Formula I or Formula II, or a stereoisomer thereof, e.g., Formula 2R,3S-I, or a pharmaceutical composition thereof, to a subject who has an immune disorder, a symptom of such a disease or a predisposition towards such a disease, with the purpose to cure, relieve, alter, affect, or prevent the immune disorder, the symptom of it, or the predisposition towards it.

In another embodiment, β-hydroxy-γ-aminophosphonates or β-amino-γ-aminophosphonates having Formula I or Formula II, or a stereoisomers thereof, or pharmaceutical compositions thereof, are used to treat allergic disorders in a subject. As used herein, the term "allergic disorder" refers to a disease, condition, or disorder associated with an allergic response against normally innocuous substances. These substances may be found in the environment (such as indoor air pollutants and aeroallergens) or they may be non-environmental (such as those causing dermatological or food allergies). Allergens can enter the body through a number of routes, including by inhalation, ingestion, contact with the skin or injection (including by insect sting). Many allergic disorders are linked to atopy, a predisposition to generate the allergic antibody IgE. Because IgE is able to sensitize mast cells anywhere in the body, atopic individuals often express disease in more than one organ. For the purpose of this disclosure, allergic disorders include any hypersensitivity that occurs upon re-exposure to the sensitizing allergen, which in turn causes the release of inflammatory mediators. Allergic disorders include without limitation, allergic rhinitis (e.g., hay fever), sinusitis, rhinosinusitis, chronic or recurrent otitis media, drug reactions, insect sting reactions, latex reactions, conjunctivitis, urticaria, anaphylaxis and anaphylactoid reactions, atopic dermatitis, asthma, and food allergies.

"Treating an allergic disorder" as used herein refers to administering a β-hydroxy-γ-aminophosphonate or β-amino-γ-aminophosphonate having Formula I or Formula II, or a stereoisomer thereof, e.g., Formula 2R,3S-I, or a pharmaceutical composition thereof, to a subject who has an allergic disorder, a symptom of such a disease or a predisposition towards such a disease, with the purpose to cure, relieve, alter, affect, or prevent the allergic disorder, the symptom of it, or the predisposition towards it.

In another embodiment, β-hydroxy-γ-aminophosphonates and β-amino-γ-aminophosphonates having Formula I or Formula II, or stereoisomers thereof, or pharmaceutical compositions thereof, are used to treat inflammatory disorders. As used herein, an "inflammatory disorder" means a disease, disorder, or condition characterized by inflammation of body tissue or having an inflammatory component. These include local inflammatory responses and systemic inflammation. Examples of such inflammatory disorders include: transplant rejection, including skin graft rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis; as well as various other diseases with significant inflammatory components, including preeclampsia; chronic liver failure, brain and spinal cord trauma, and cancer. There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used in cancer chemotherapy.

"Treating an inflammatory disorder" as used herein refers to administering a β-hydroxy-γ-aminophosphonate or β-amino-γ-aminophosphonate having Formula I or Formula II, or a stereoisomer thereof, e.g., Formula 2R,3S-I, or a pharmaceutical composition thereof, to a subject who has an inflammatory disorder, a symptom of such a disorder or a predisposition towards such a disorder, with the purpose to cure, relieve, alter, affect, or prevent the inflammatory disorder, the symptom of it, or the predisposition towards it.

Exemplary immune, allergic, and/or inflammatory disorders include arthritis, type 1 insulin-dependent diabetes mellitus, adult respiratory distress syndrome, inflammatory bowel disease, dermatitis, meningitis, thrombotic thrombocytopenic purpura, Sjogren's syndrome, encephalitis, uveitis, leukocyte adhesion deficiency, rheumatoid arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, tissue specific autoimmunity, degenerative autoimmunity delayed hypersensitivities, autoimmune complications of AIDS, atrophic gastritis, ankylosing spondylitis and Addison's disease.

In another embodiment, β-hydroxy-γ-aminophosphonates and β-amino-γ-aminophosphonates having Formula I or Formula II, or stereoisomers thereof, or pharmaceutical compositions thereof, are used to treat a disease, condition, or disorder mediated by the lymphocyte count in the blood of a subject, e.g., acute or chronic rejection of cell, tissue or organ allo- or xenografts or delayed graft function, graft versus host disease, autoimmune diseases, e.g., rheumatoid arthritis, systemic lupus erythematosus, hashimoto's thyroidis, multiple sclerosis, myasthenia gravis, neuropathic pain. Behcet's disease, Wegener's granulamatosis, ankylosing spondylitis, polymyositis, CIDP (Chronic Idiopathic Demyelinating Polyneuropathy), diabetes type I or II and the disorders associated therewith, vasculitis, pernicious anemia, Sjoegren syndrome, uveitis, psoriasis, Graves ophthalmopathy, alopecia greata and others, allergic diseases, e.g. allergic asthma, atopic dermatitis, allergic rhinitis/conjunctivitis, allergic contact dermatitis, inflammatory diseases optionally with underlying aberrant reactions, e.g., inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g., myocardial infarction, stroke, gut ischemia, renal failure or hemorrhage shock, traumatic shock, cancer, e.g., breast cancer, T cell lymphomas or T cell leukemias, infectious diseases, e.g., toxic shock (e.g., superantigen induced), septic shock, adult respiratory distress syndrome or viral infections, e.g., AIDS, viral hepatitis, e.g., hepatitis B or C, chronic bacterial infection, or neurodegenerative diseases, e.g., Alzheimer disease, amyotrophic lateral sclerosis or senile dementia. Examples of cell, tissue or solid organ transplants include e.g., pancreatic islets, stem cells, bone marrow, corneal tissue, neuronal tissue, heart, lung, combined heart-lung, kidney, liver, bowel, pancreas, trachea or esophagus.

In another embodiment, β-hydroxy-γ-aminophosphonates and β-amino-γ-aminophosphonates having Formula I or Formula II, or stereoisomers thereof, or pharmaceutical compositions thereof, are used to treat a T-cell mediated disease in a subject. The term "T-cell mediated disease" as used herein refers to a condition or disorder selected from the group consisting of graft rejection, graft versus host disease, unwanted delayed-type hypersensitivity reactions (such as delayed-type allergic reactions), T-cell mediated pulmonary diseases, and autoimmune diseases. T-cell mediated pulmonary diseases include sarcoidosis, hypersensitivity pneumonitis, acute interstitial pneumonitis, alveolitis, pulmonary fibrosis, idiopathic pulmonary fibrosis and other diseases characterized by inflammatory lung damage. Autoimmune diseases include multiple sclerosis, neuritis, polymyositis, psoriasis, vitiligo, Sjogren's syndrome, rheumatoid arthritis, Type 1 diabetes, autoimmune pancreatitis, inflammatory bowel diseases (e.g., Crohn's disease and ulcerative colitis), celiac disease, glomerulonephritis, scleroderma, sarcoidosis, autoimmune thyroid diseases (e.g., Hashimoto's thyroiditis and Graves disease), myasthenia gravis, Addison's disease, autoimmune uveoretinitis, pemphigus vulgaris, primary biliary cirrhosis, pernicious anemia, and systemic lupus erythematosis.

In another embodiment, β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, are administered to modulate an immune response in a subject.

In another embodiment, β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, are administered to a subject to modulate the degree of fat accumulation in the liver of the subject. In another embodiment, administering β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, to a subject decreases fat accumulation in the liver of the subject. In another embodiment, administering β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, to a subject decreases fat accumulation in the liver of a subject by about 5% to about 100%, e.g., by about 5% to about 50%, e.g., by about 10% to about 40%. In another embodiment, administering β-hydroxy-γ-aminophosphonates and β-amino-γ-aminophosphonates having Formula I or Formula II, or pharmaceutically acceptable hydrates, crystalline forms or amorphous forms thereof, or pharmaceutical compositions thereof, to a subject decreases the fat accumulation in the liver of the subject by about 5%, about 10%, about 15%, about 20%, about 25%, about 30%, about 35%, about 40%, about 45%, about 50%, about 55%, about 60%, about 65%, about 70%, or about 75%, or more.

In another embodiment, β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, are administered to modulate the levels of alanine ALT, AST, and/or AP in a subject. In another embodiment, administering β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, to a subject decreases the levels of ALT, AST, and/or AP in the subject. In another embodiment, administering β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, to a subject decreases the levels of ALT, AST, and/or AP in the subject by about 5% to about 100%, e.g., by about 5% to about 50%, e.g., by about 10% to about 40%. In another embodiment, administering β-hydroxy-γ-aminophosphonates and β-amino-γ-aminophosphonates having Formula I or Formula II, or pharmaceutically acceptable hydrates, crystalline forms or amorphous forms thereof, or pharmaceutical compositions thereof, to a subject decreases the levels of ALT, AST, and/or AP in the subject by about 5%, about 10%, about 15%, about 20%, about 25%, about 30%, about 35%, about 40%, about 45%, about 50%, about 55%, about 60%, about 65%, about 70%, or about 75%, or more. The levels of ALT, AST, and/or AP in a subject can be determined using methods well known by those skilled in the art.

In another embodiment, β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, are administered to a subject to modulate the levels of glucose, cholesterol, and/or triglycerides in the subject. In another embodiment, administering β-hydroxy-γ-aminophosphonates and β-amino-γ-aminophosphonates having Formula I or Formula II, or pharmaceutically acceptable hydrates, crystalline forms or amorphous forms thereof, or pharmaceutical compositions thereof, to a subject decreases the levels of glucose, cholesterol, and/or triglycerides in the subject. In another embodiment, administering β-hydroxy-γ-aminophosphonates and β-amino-γ-aminophosphonates having Formula I or Formula II, or pharmaceutically acceptable hydrates, crystalline forms or amorphous forms thereof, or pharmaceutical compositions thereof, to a subject decrease the levels of glucose, cholesterol, and/or triglycerides in the subject by about 5% to about 100%, e.g., by about 5% to about 50%, e.g., by about 10% to about 40%. In another embodiment, administering β-hydroxy-γ-aminophosphonates and β-amino-γ-aminophosphonates having Formula I or Formula II, or pharmaceutically acceptable hydrates, crystalline forms or amorphous forms thereof, or pharmaceutical compositions thereof, to a subject decreases the level of glucose, cholesterol, and/or triglycerides in the subject by about 5%, about 10%, about 15%, about 20%, about 25%, about 30%, about 35%, about 40%, about 45%, about 50%, about 55%, about 60%, about 65%, about 70%, or about 75%, or more. The levels of glucose, cholesterol, and/or triglycerides in a subject can be determined using methods well known by those skilled in the art.

In another embodiment, β-hydroxy-γ-aminophosphonate or β-amino-γ-aminophosphonate having Formula I or Formula II, or a stereoisomer thereof, or pharmaceutically acceptable hydrates, crystalline forms or amorphous forms thereof, or pharmaceutical compositions thereof, are administered to treat liver damage or disease in a subject.

In another embodiment, β-hydroxy-γ-aminophosphonate or β-amino-γ-aminophosphonate having Formula I or Formula II, or a stereoisomer thereof, or pharmaceutically acceptable hydrates, crystalline forms or amorphous forms thereof, or pharmaceutical compositions thereof, are administered to provide hepatoprotection in a subject.

"Providing hepatoprotection" as used herein refers to administering a β-hydroxy-γ-aminophosphonate or β-amino-γ-aminophosphonate having Formula I or Formula II, or a stereoisomer thereof, e.g., Formula 2R,3S-I, or a pharmaceutical composition thereof, to a subject to reduce or prevent damage to the liver of the subject. For example, providing hepatoprotection by administering a compound having Formula I or Formula II, or stereoisomer thereof, to subject may reduce or prevent the toxic action of a therapeutic agent e.g., an anticancer agent, on the liver, and lead to a decrease in acute toxicity and/or to less pronounced manifestations of hepatotoxicity normally caused by the therapeutic agent. Providing hepatoprotection by administering a compound having Formula I or Formula II, or stereoisomer thereof, to subject may also reduce or prevent the liver damage normally associated with obesity and/or other pathological diseases, disorders, or conditions known to cause liver damage.

In another embodiment, β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, are administered to a subject to modulate a combination physiological responses, e.g., increase the level of $T_{reg}$ cells and decrease the level ALT in a subject.

In another embodiment, β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, are administered to a subject to inhibit the effect LPS in a subject.

In another embodiment, β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, are administered to a subject to induce cell proliferation in a subject.

In another embodiment, β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, are administered to a subject to induce phagocytosis in a subject.

In another embodiment, β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, are administered to a subject to reduce mycetoma development in a subject.

In another embodiment, β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, or pharmaceutical compositions thereof, are administered to a subject in combination with one or more additional therapeutic agents or treatments.

In another embodiment, β-hydroxy-γ-aminophosphonates or β-amino-γ-aminophosphonates having Formula I or Formula II, or stereoisomers thereof, or pharmaceutically acceptable hydrates, crystalline forms or amorphous forms thereof, are administered to a subject as part of a pharmaceutical composition comprising a β-hydroxy-γ-aminophosphonate or β-amino-γ-aminophosphonate having Formula I or Formula II, or stereoisomer thereof, and one or more pharmaceutically acceptable carriers.

The approximate dosage form(s), mode(s) of administration, dosage amounts, and dosing regimen(s) for use in these methods include those described herein, although additional suitable dosage forms, modes of administration, dosage amounts and dosing regimens will be familiar to those of ordinary skill in the relevant arts and/or can be empirically determined by the clinical practitioner using routine methods known to the ordinarily skilled artisan based on the guidance provided herein and in view of the information that is readily available in the art.

Compositions within the scope of the present disclosure include all compositions wherein one or more of the compounds of the present disclosure are contained in an amount which is effective to achieve its intended purpose. While individual needs vary, determination of optimal ranges of effective amounts of each component is within the expertise of those of ordinary skill in the art. Typically, the compounds may be administered to mammals, e.g., humans, orally at a dose of about 0.0025 to about 50 mg/kg, or an equivalent amount of the pharmaceutically acceptable salt or ester thereof. For example, about 0.01 to about 25 mg/kg can be orally administered to treat, ameliorate, or prevent such disorders. For intramuscular injection, the dose is generally about one-half of the oral dose, for example, a suitable intramuscular dose would be about 0.0025 to about 25 mg/kg, e.g., from about 0.01 to about 5 mg/kg.

Compositions with the scope of the present disclosure also include all compositions wherein one or more of the compounds of the present disclosure are combined with one or more additional therapeutic agents (e.g., immunomodulating agents, anti-inflammatory agents, anti-allergic agents, AIDS treatment agents) in therapeutically effective amounts. In addition to active agents (e.g., one or more compounds of the disclosure and one or more additional therapeutic agents), such compositions can optionally comprise one or more pharmaceutical excipients well-known in the relevant arts. Typically, such compositions are administered orally. The optimal amounts of each active agent in the composition can be determined by the clinical practitioner using routine methods known to the ordinarily skilled artisan based on the guidance provided herein and in view of the information that is readily available in the art.

The unit oral dose may comprise from about 0.01 to about 1000 mg, e.g., about 0.1 to about 100 mg of the compound. The unit dose may be administered one or more times daily as one or more tablets or capsules or other suitable form, each containing from about 0.1 to about 10, conveniently about 0.25 to 50 mg of the compound.

In a topical formulation, the compound may be present at a concentration of about 0.01 to 100 mg per gram of carrier. In one embodiment, the compound is present at a concentration of about 0.07-1.0 mg/ml, e.g., about 0.1-0.5 mg/ml, e.g., about 0.4 mg/ml.

In addition to administering the compound to the subject as a raw chemical, the compounds of the disclosure may be administered as part of a pharmaceutical composition comprising one or more suitable pharmaceutically acceptable carriers, such as one or more excipients or auxiliaries which facilitate processing of the compounds into preparations which can be used pharmaceutically. Preferably, such pharmaceutical compositions contain from about 0.01 to 99 percent, e.g., from about 0.25 to 75 percent of active compound(s), together with the excipient(s), particularly those compositions which can be administered orally or topically and which can be used for the preferred type of administration, such as tablets, dragees, slow release lozenges and capsules, mouth rinses and mouth washes, gels, liquid suspensions, and also preparations which can be administered rectally, such as suppositories, as well as suitable solutions for administration by parenteral administration, e.g., via intravenous infusion, intramuscular or subcutaneous injection.

The pharmaceutical compositions of the disclosure may be administered to any subject who may experience the beneficial effects of the compounds and/or compositions of the disclosure. Foremost among such subjects are humans, although the disclosure is not intended to be so limited. Other subjects include veterinary animals (cows, sheep, pigs, horses, dogs, cats and the like).

The compounds and pharmaceutical compositions of the disclosure may be administered to a subject by any means that achieve their intended purpose. For example, administration may be by parenteral, subcutaneous, intravenous, intramuscular, intradermal, intraperitoneal, transdermal, buccal, sublingual, intrathecal, intracranial, intranasal, ocular, pulmonary (e.g., via inhalation) or topical routes. Alternatively, or concurrently, administration may be by the oral route. The dosage administered will be dependent upon the age, health, and weight of the recipient, kind of concurrent treatment, if any, frequency of treatment, and the nature of the effect desired.

Suitable oral pharmaceutical compositions of the present disclosure are manufactured in a manner which is itself well-known in the art, for example, by means of conventional mixing, granulating, dragee-making, dissolving, or lyophilizing processes. Thus, solid pharmaceutical preparations for oral use can be obtained by combining one or more of the compounds of the disclosure and optionally one or more additional active pharmaceutical ingredients with one or more solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose, sucrose, fructose and the like; sugar alcohols such as mannitol, sorbitol, or xylitol and the like; cellulose preparations and/or calcium phosphates, for example tricalcium phosphate or calcium hydrogen phosphate; as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or poly(ethylene glycol). Dragee cores are provided with suitable coatings which, if desired, are resistant to gastric juices. For this purpose, concentrated saccharide solutions may be used, which may optionally contain gum arabic, talc, polyvinyl pyrrolidone, poly(ethylene glycol) and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, can be used. Dye stuffs or pigments may be added to the tablets or dragee coatings, for example, for identification or in order to characterize combinations of active ingredients or doses thereof.

Other pharmaceutical preparations which can be used orally include push-fit capsules made of gelatin, as well as soft, sealed capsules made of gelatin and a plasticizer such as glycerol or sorbitol. In certain embodiments, the push-fit capsules can comprise one or more of the compounds of the disclosure in the form of granules which may be mixed with fillers such as lactose, binders such as starches, and/or lubricants such as talc or magnesium stearate and, optionally, stabilizers. In soft capsules, one or more pharmaceutical ingredients (e.g., one or more compounds of the disclosure and optionally one or more additional active pharmaceutical ingredients) are preferably dissolved or suspended in suitable liquids, such as fatty oils, or liquid paraffin. In addition, stabilizers may be added.

Additional suitable pharmaceutical preparations comprising compounds of the present disclosure are disclosed in U.S. Pat. No. 8,178,515 and Gomez-Solis et al., *Pharmacology* 88:10-17 (2011).

In certain embodiments, a pharmaceutical composition comprising a compound of the disclosure and one or more additional therapeutic agents are administered to the subject.

In certain embodiments, compounds of the disclosure and one or more additional therapeutic agents are administered to the subject in separate compositions under one or more of the following conditions: at different periodicities, at different durations, at different concentrations, by different administration routes, etc. In one such embodiment, the compound of Formula I is administered prior to the one or more additional therapeutic agents, e.g., 0.5, 1, 2, 3, 4, 5, 10, 12, or 18 hours, 1, 2, 3, 4, 5, or 6 days, 1, 2, 3, or 4 weeks prior to the administration of the therapeutic agent(s). In another such embodiment, the compound is administered after the one or more additional therapeutic agents, e.g., 0.5, 1, 2, 3, 4, 5, 10, 12, or 18 hours, 1, 2, 3, 4, 5, or 6 days, 1, 2, 3, or 4 weeks after the administration of the therapeutic agent(s). In another such embodiment, the compound of Formula I and the one or more additional therapeutic agents are administered concurrently but on different schedules, e.g., the compound of Formula I is administered daily while the one or more additional therapeutic agents are administered once every two days, once every three days, once every four days, once every five days, once every six days, once a week, once every two weeks, once every three weeks, once every four weeks, etc.

EXAMPLE 1

T Cell Levels in Normal Rats

The ability of (2R,3S)-(2-hydroxy-5-methyl-3-trimethylammonium-hexyl)-phosphonic acid; iodide (referred to herein as "Compound 1") to modify the level of blood lymphocytes in rats was investigated. (2R,3S)-(2-hydroxy-5-methyl-3-trimethylammonium-hexyl)-phosphonic acid; iodide (22.4 mg/kg) was administered to Wistar rats 5 days a week for two weeks. The circulating lymphocyte populations were identified and quantified by flow cytometry mice monoclonal antibodies against rat CD3+ conjugated with different fluorochromes and analyzed on a FACS Calibur flow cytometer BD using the Cell Quest software. As shown in FIG. 1, treatment with Compound 1 increased the level of total T-lymphocytes as compared to control group. It is noted that administration of Compound 1 increases the levels of T helper (CD4+) and cytotoxic (CD8+) lymphocytes. In addition, an increase in regulatory T cells (CD4+CD25+) ($p<0.01$) was observed.

EXAMPLE 2

T Cell Levels in Obese Rats

The effect of (2R,3S)-(2-hydroxy-5-methyl-3-trimethylammonium-hexyl)-phosphonic acid dimethyl ester, iodide (referred to herein as "Compound 2") on the levels of T-lymphocytes in blood in obese rats as compared to normal animals was investigated. Obesity is characterized by chronic low-grade inflammation, which has been associated with changes in blood T-lymphocyte levels.

Figure 2:
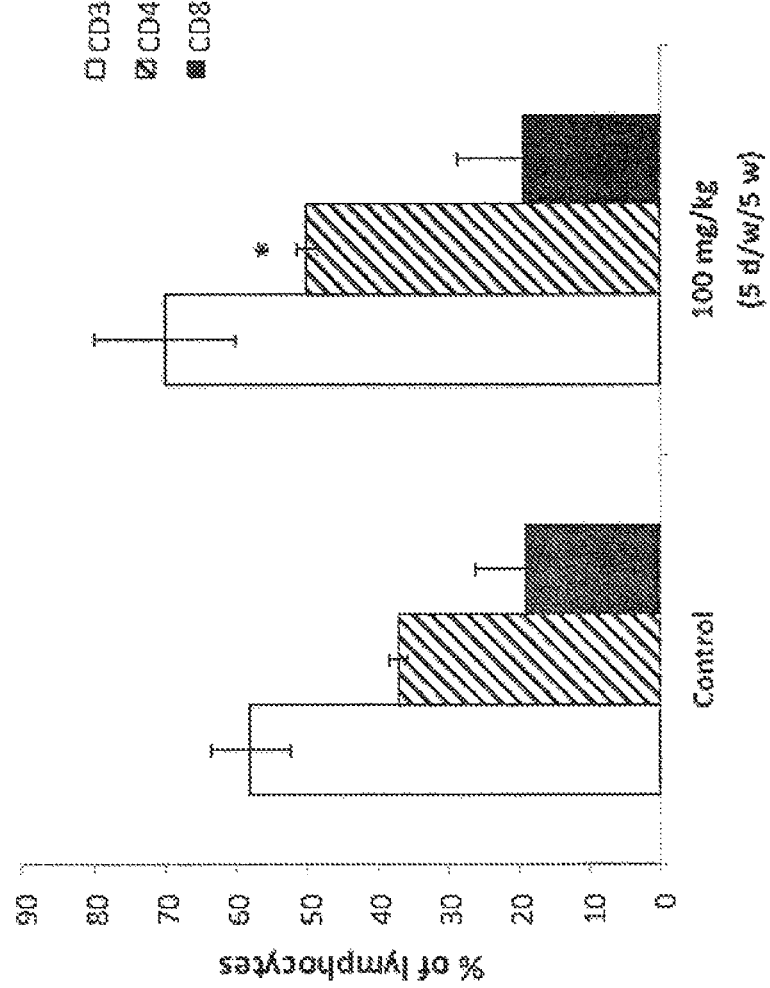
FIG. 2 is a bar graph showing the effect of (2R,3S)-(2-hydroxy-5-methyl-3-trimethylammonium-hexyl)-phosphonic acid dimethyl ester; iodide (100 mg/kg) on lymphocyte levels in obese (fa/fa) Zucker rats (ZDF) and lean rats treated by five weeks. * p<0.01 compared to control group.

Compound 2 (100 mg/kg) was administered to obese (fa/fa) Zucker rats five days a week for 5 weeks. As shown in FIG. 2, treatment with Compound 1 increased the level of total blood T-lymphocytes as compared to control group. The level of T helper (CD4+) increased; cytotoxic T-lymphocyte(CD8+) levels remained unchanged.

EXAMPLE 3

T Cell Levels in Normal and Obese Rats

The effect of Compound 2 on T lymphocyte populations in normal and unhealthy rats was investigated. Obese (fa/fa) Zucker rats (ZDF) and lean Wistar rats, as control, were used. Zucker rats present a mutation in the leptin receptor, which is the molecular basis of their characteristic phenotype (loss of satiety). Obese Zucker rats are considered representative of obesity-associated type diabetes in humans. They are hyperlipidaemic, grossly obese, hyperinsulinaemic, insulin resistant, and not prone to ketosis. Metabolic changes related to increased insulin resistance, including oxidative stress, have been implicated in obesity-related pathophysiology. However, most attention in recent years has been devoted to the concept that obesity elicits a chronic low-grade systemic inflammatory state.

Modulation of the immune system by leptin is exerted at the development, proliferation, anti-apoptotic, maturation, and activation levels. In fact, leptin receptors have been found in neutrophils, monocytes, and lymphocytes, and the leptin receptor belongs to the family of class I cytokine receptors. The overall leptin action in the immune system is a pro-inflammatory effect, activating pro-inflammatory cells, promoting T-helper responses.

In this study, animals were treated with 100 mg/kg of Compound 2 five days a week for 5 weeks. The circulating lymphocyte populations were identified and quantified by flow cytometry using mice monoclonal antibodies against rat CD3+ conjugated with different fluorochromes and analyzed on a FACS Calibur flow cytometer BD using the Cell Quest software. The results show that obese Zucker rats treated with Compound 2 have an increase in T cell populations similar to that performed in healthy Wistar rats, although in minor intensity.

EXAMPLE 4

T Cell Levels in Normal and Obese Rats

To determine whether the increase in lymphocytes is due to an increased production of lymphocytes or their mobility, the levels of T lymphocyte subpopulations in bloodstream, thymus, and spleen from obese (fa/fa) Zucker rats (ZDF) and lean rats (control), after 8 weeks of treatment with Compound 2 was investigated.

T cell maturation starts from pro-lymphocytes in thymus from bone marrow and are identified as double negative, because they do not express CD4 and CD8 co-receptors. Then they are converted into double positive, because they express both co-receptors, and finally become CD4+ or CD8+ and leave to bloodstream to target secondary lymphoid organs (spleen and lymph).

Figure 3:
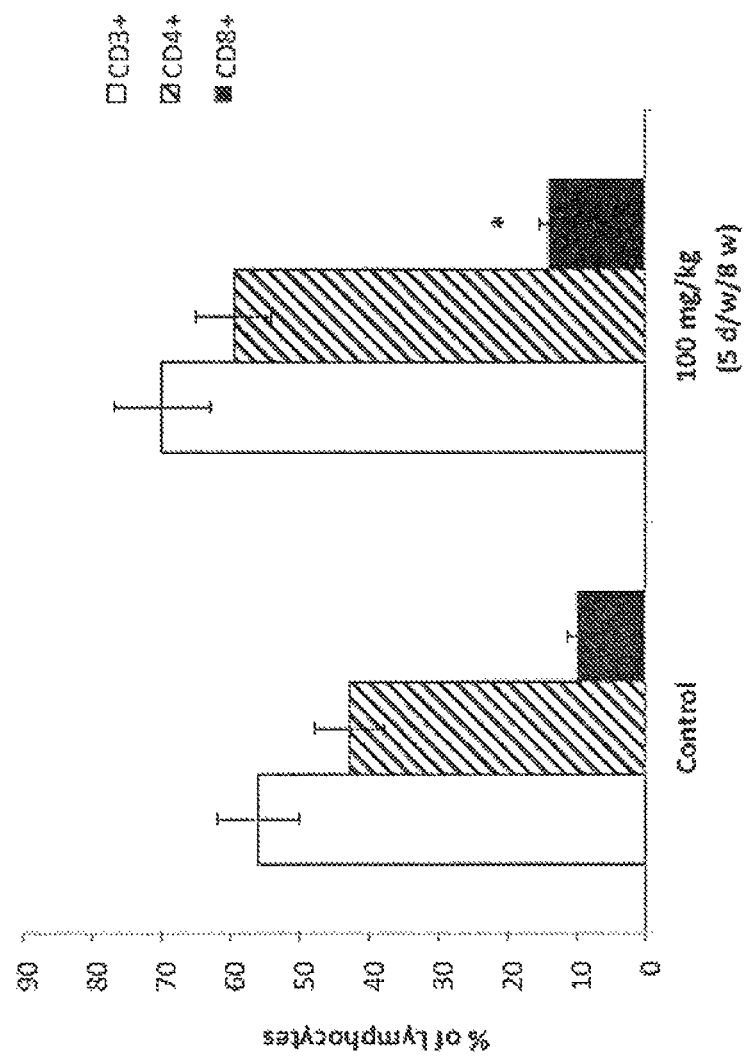
FIG. 3 is a bar graph showing the effect of (2R,3S)-(2-hydroxy-5-methyl-3-trimethylammonium-hexyl)-phosphonic acid dimethyl ester; iodide (100 mg/kg) on lymphocyte levels in obese (fa/fa) Zucker rats (ZDF) and lean rats treated by eight weeks. Each value represents the mean±SD of six animals. * p<0.01 compared to control group.

Obese rats were used in this study. Lymphocyte populations from bloodstream, thymus, and spleen were identified and quantified by flow cytometry using mice monoclonal antibodies against rat CD3+ conjugated with different fluorochromes and analyzed on a FACS Calibur flow cytometer BD using the Cell Quest software. The results show that Compound 2 (100 mg/kg) increased the levels of total blood lymphocytes levels (FIG. 3). A significant increase was also observed in cytotoxic lymphocytes.

Figure 4:
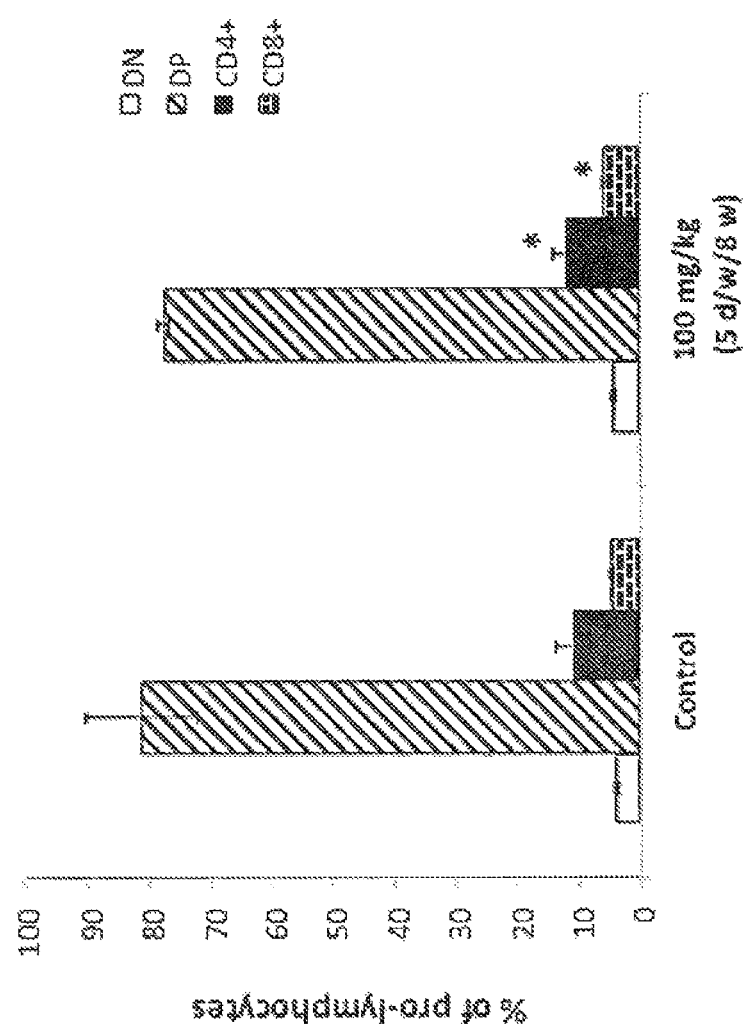
FIG. 4 is a bar graph showing the effect of (2R,3S)-(2-hydroxy-5-methyl-3-trimethylammonium-hexyl)-phosphonic acid dimethyl ester; iodide (100 mg/kg) on subpopulations of pro-lymphocytes in thymus from obese (fa/fa) Zucker rats (ZDF) and lean rats treated by eight weeks. Each value represents the mean±SD of six animals. * p<0.01 compared to control group.

In the thymus of treated animals, a slight increase of the population of double double negative CD4−CD8− (DN) lymphocytes, and a slight decrease of the double positive CD8+ CD4+ (DP) lymphocytes was observed. In addition, an increase in the population of helper T cells and an increase in the cytotoxic T-lymphocytes was observed (FIG. 4). The increase in lymphocytes double negative, the reduction in double positive cells, and the increase of CD4+ and CD8+ suggests that administration of Compound 2 promotes the maturation of T-lymphocytes. The increase in circulating lymphocytes could be due to this effect.

Figure 5:
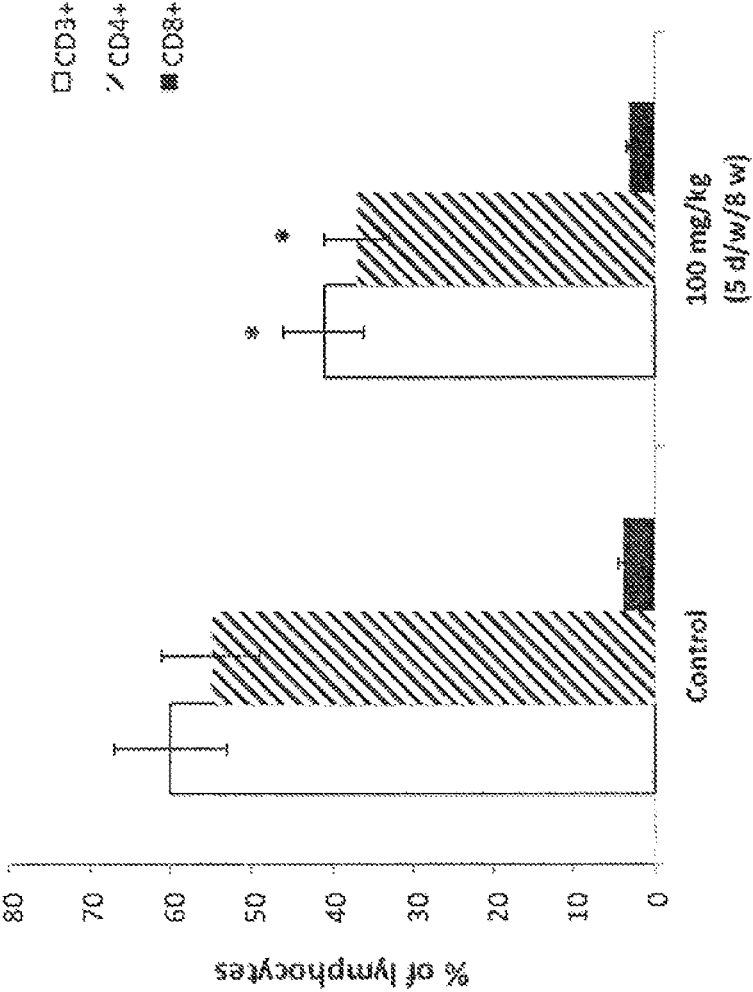
FIG. 5 is a bar graph showing the effect of (2R,3S)-(2-hydroxy-5-methyl-3-trimethylammonium-hexyl)-phosphonic acid dimethyl ester; iodide (100 mg/kg) on populations of lymphocytes in spleen from obese (fa/fa) Zucker rats (ZDF) and lean rats treated by eight weeks. Each value represents the mean±SD of six animals. * p<0.01 compared to control group.

T-lymphocyte subpopulations in the spleen of treated animals showed a decline of total T-lymphocytes present in this organ. In addition, a reduction in subpopulations of T helper cells and in cytotoxic lymphocytes was observed (FIG. 5). The decrease in lymphocyte subpopulations may be due to no entry of new cells or to the output of these cells into bloodstream.

EXAMPLE 5

Histological Studies of Thymus and Spleen Tissue

Obesity compromises the mechanisms regulating T-cell generation by inducing premature thymic involution and defects in thymic function. Obesity accelerates the age-related reduction of T-cell receptor (TcR) excision circle bearing peripheral lymphocytes, an index of recently generated T cells from thymus. Hypoplasia and atrophy of lymphoid follicles has been also observed in the spleen from obese subjects, which is associated with absent of typical pattern of structure and germinal centers.

Figure 6:
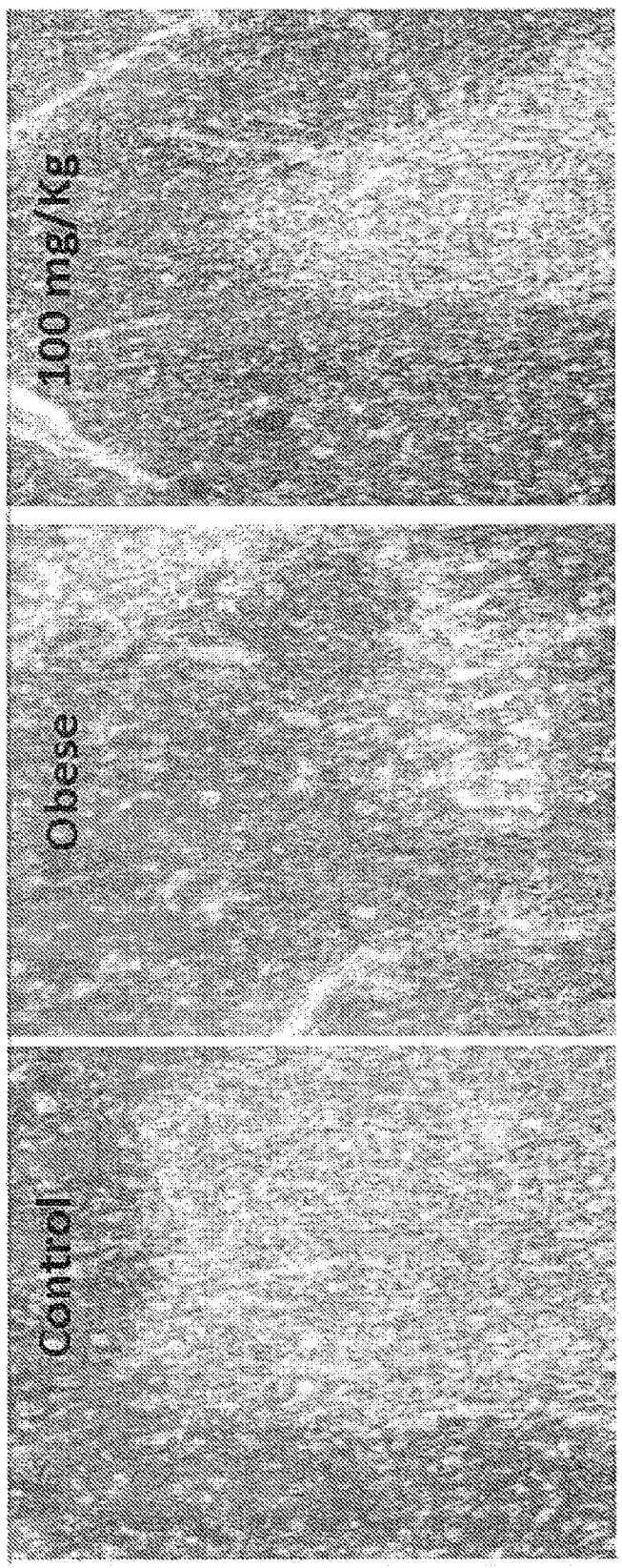
FIG. 6 is a series of three images showing the effect of (2R,3S)-(2-hydroxy-5-methyl-3-trimethylammonium-hexyl)-phosphonic acid dimethyl ester; iodide (100 mg/kg) on structural morphology from thymus slices obtained from obese (fa/fa) Zucker rats (ZDF) and lean rats treated by five weeks. Each value represents the mean±SD of six animals.
Figure 7:
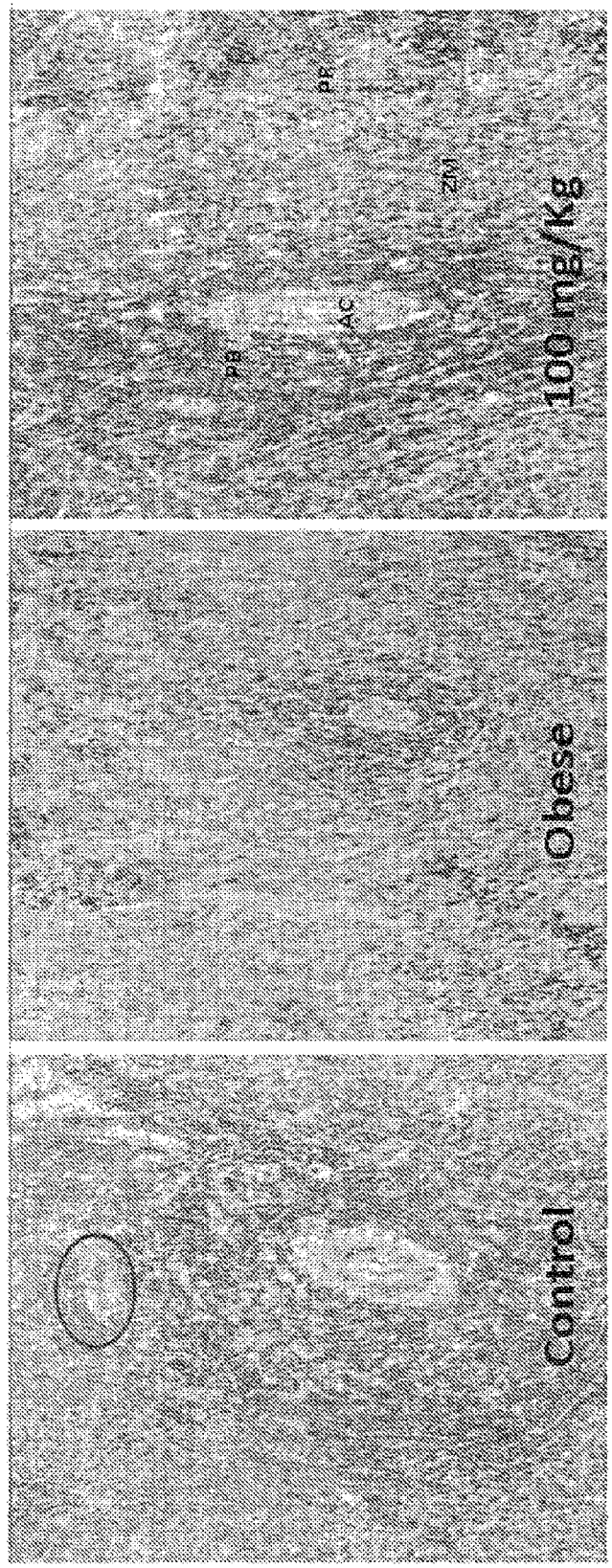
FIG. 7 is a series of three images showing the effect of (2R,3S)-(2-hydroxy-5-methyl-3-trimethylammonium-hexyl)-phosphonic acid dimethyl ester; iodide (100 mg/kg) on structural morphology from spleen slices obtained from obese (fa/fa) Zucker rats (ZDF) and lean rats treated by five weeks. Each value represents the mean±SD of six animals.

Samples of tissue from thymus (FIG. 6) and spleen (FIG. 7) were taken and histological sections were made and stained with hematoxylin and eosin from obese (fa/fa) Zucker rats and lean rats. The histological sections from thymus show a decrease in thymic medulla in samples from obese animals. When animals were treated with Compound 2 for five weeks, a recovery of the cellularity of medulla in this lymphoid organ was observed.

In spleen, a decrease in the white pulp and the area of lymphoid follicles was reduced in obese Zucker rats. Animals treated with Compound 2 showed a recovery of morphology.

EXAMPLE 6

Histological Studies of Liver Tissue

The ability of Compound 2 (100 mg/kg) to modify the liver injury present in obese (fa/fa) Zucker rats (ZDF) was investigated. Obese (fa/fa) Zucker rats (ZDF) and lean rats, as control, were used. Obese (fa/fa) Zucker rats (ZDF) were treated with a daily dose of 100 mg/kg of the Compound 2, 5 days a week during eight weeks.

Obesity is the most significant single risk factor for the development of fatty liver disease, both in children and in adults. Obesity is also predictive of the presence of fibrosis, potentially progressing into advanced liver disease. From a pathogenic point of view, insulin resistance plays a central role in the accumulation of triglycerides inside the hepatocytes and the initiation of the inflammatory cascade.

Figure 8:
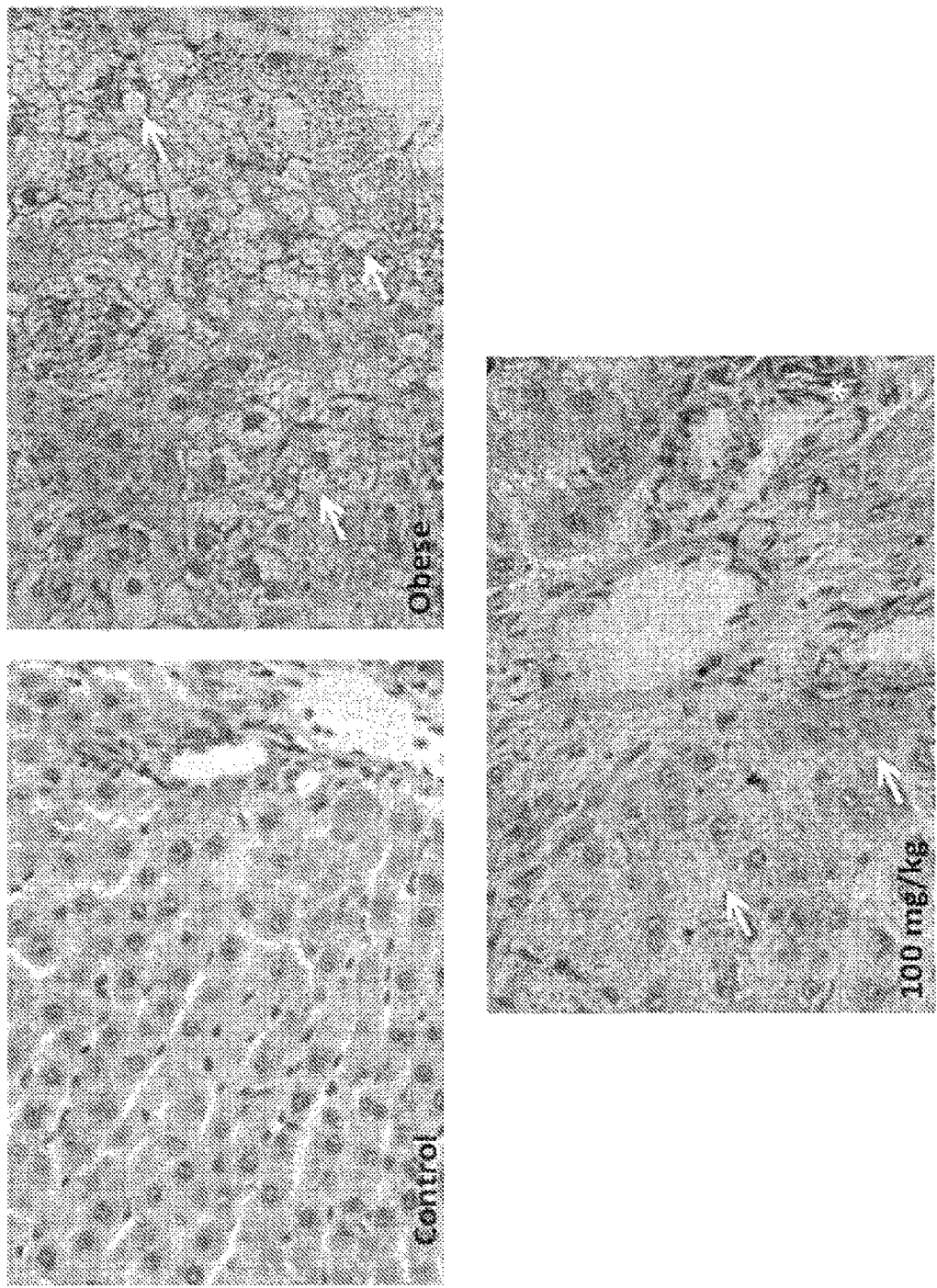
FIG. 8 is a series of three images showing the effect of (2R,3S)-(2-hydroxy-5-methyl-3-trimethylammonium-hexyl)-phosphonic acid dimethyl ester; iodide (100 mg/kg) on structural morphology from liver slices obtained from obese (fa/fa) Zucker rats (ZDF) and lean rats treated for five weeks. * p<0.01 compared to control group.

Samples of tissue from liver were taken, and histological sections were made and stained with hematoxylin and eosin from obese (fa/fa) Zucker rats and lean rats. When histological sections from liver were analyzed, it was found that obese Zucker rats showed hepatocellular injury characterized by centrilobular, microvesicular fatty infiltration, and hepatocytes with ballooning degeneration and pleomorphic nuclei, and these changes were accompanied by modifications in liver function. Animals were treated with Compound 2 (100 mg/kg) for five days a week for eight weeks showed significant reduction in the degree of fat accumulation in the liver, and the specimens displayed normal liver histology and scattered inflammatory cells (FIG. 8).

EXAMPLE 7

Level of Liver Enzymes

To determine whether the morphological changes in liver tissue (see EXAMPLE 6) were associated with an improvement in liver function, the levels of liver enzymes were investigated. Obese (fa/fa) Zucker rats (ZDF) and lean rats, as control, were used. Obese (fa/fa) Zucker rats (ZDF) were treated with a daily dose of Compound 2 (100 mg/kg) 5 days a week during eight weeks.

Plasma from blood samples was collected and liver enzymes were quantified by colorimetric methods. Liver enzymes, or liver (hepatic) function tests, are used to determine if the liver is functioning normally, or if it has an injury or disease. Alanine aminotransferase (ALT) is typically used to detect a liver injury or an active or chronic liver problem. Aspartate aminotransferase (AST) is used to detect liver injuries and long-term liver disease. Highly elevated levels of AST may indicate active hepatitis from any cause. Alkaline phosphatase (ALP) is an enzyme found in the bile ducts of the liver. Damage or obstruction of the bile ducts may result in elevated levels of ALP. Obese Zucker rats showed an increase in ALT, AST and ALP activities in serum.

Figure 9:
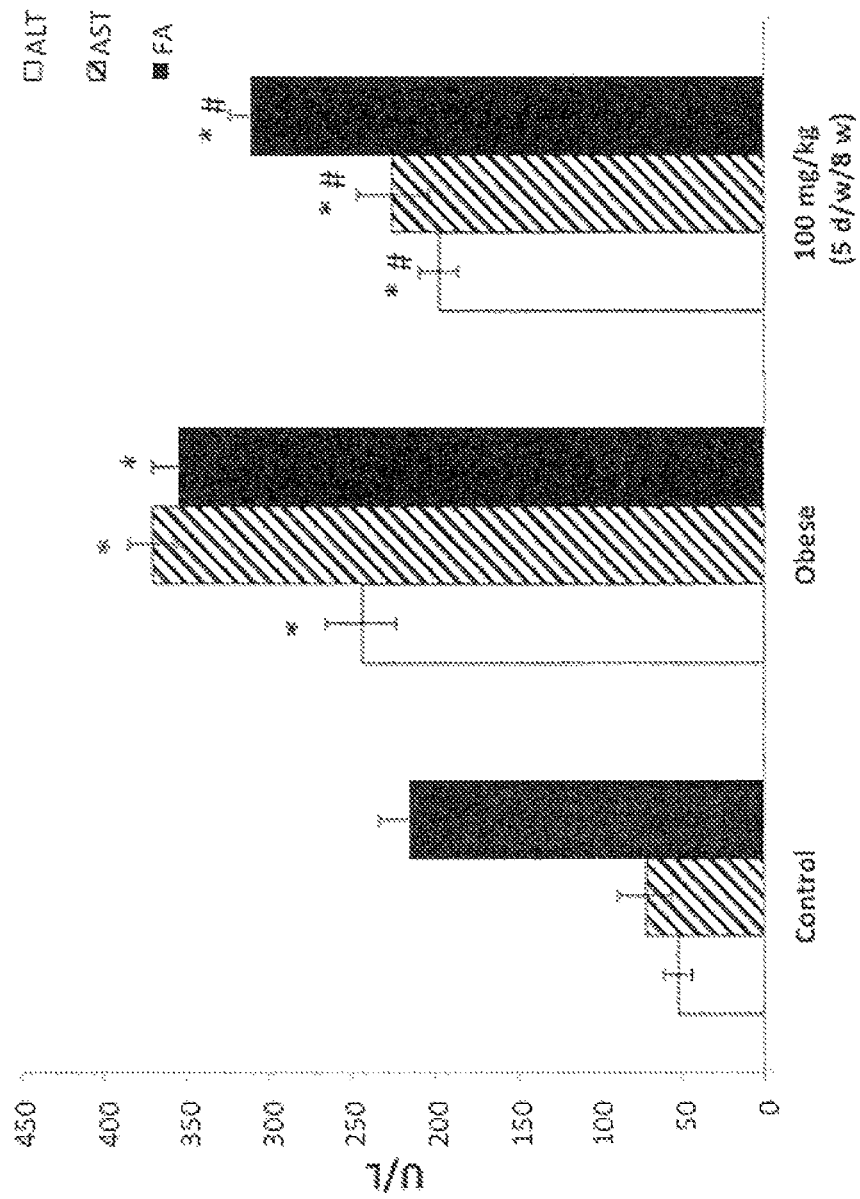
FIG. 9 is a bar graph showing the effect of (2R,3S)-(2-hydroxy-5-methyl-3-trimethylammonium-hexyl)-phosphonic acid dimethyl ester; iodide (100 mg/kg) on serum liver enzymes from obese (fa/fa) Zucker rats (ZDF) and lean rats treated for five weeks. * p<0.01 compared to control group.

It was found that rats treated with 100 mg/kg of Compound 2 produced a significant reduction in the levels of ALT, AST and AP in serum ($p<0.01$). These results are indicative of a prevention of liver damage (FIG. 9).

EXAMPLE 8

Level of Glucose, Triglycerides, and Cholesterol

To determine whether the morphological and functional changes (see EXAMPLES 6 and 7) were associated with an improvement in liver metabolism, the levels of glucose, triglycerides and cholesterol were quantified. Obese (fa/fa) Zucker rats (ZDF) and lean rats, as control, were used. Obese (fa/fa) Zucker rats (ZDF) were treated with a daily dose of Compound 2 (100 mg/kg) 5 days a week during eight weeks. Plasma from blood samples was collected, and the triglycerides, cholesterol and glucose levels were quantified by colorimetric methods. Also, liver samples were taken, and liver glycogen was measured.

The liver is one of the most important organs in the body, and serves a variety of important functions including metabolic, vascular, immunological, secretory, and excretory functions. It plays a key role in the carbohydrate, protein, and fat metabolism in the human body, when there is an excess of carbohydrates in liver can be stored as glycogen deposits, which can be reconverted to glucose according to need (glycogenesis and glycogenolysis). Most mammalian cells store glycogen as a reserve for the production of glucose 6-phosphate as a metabolic fuel for glycolysis. In the liver, glycogen is mainly stored as a glucose reservoir for other tissues. There is ample evidence that humans with type 2 diabetes suffer from excess hepatic glucose production, and an abnormal hepatic glycogen metabolism. Studies with Zucker rats have also shown dramatic findings relate to regarding abnormal glycogen synthesis and storage. Obese Zucker rats showed an increase in glucose, triglycerides, and cholesterol levels in liver ($p<0.05$).

Figure 10:
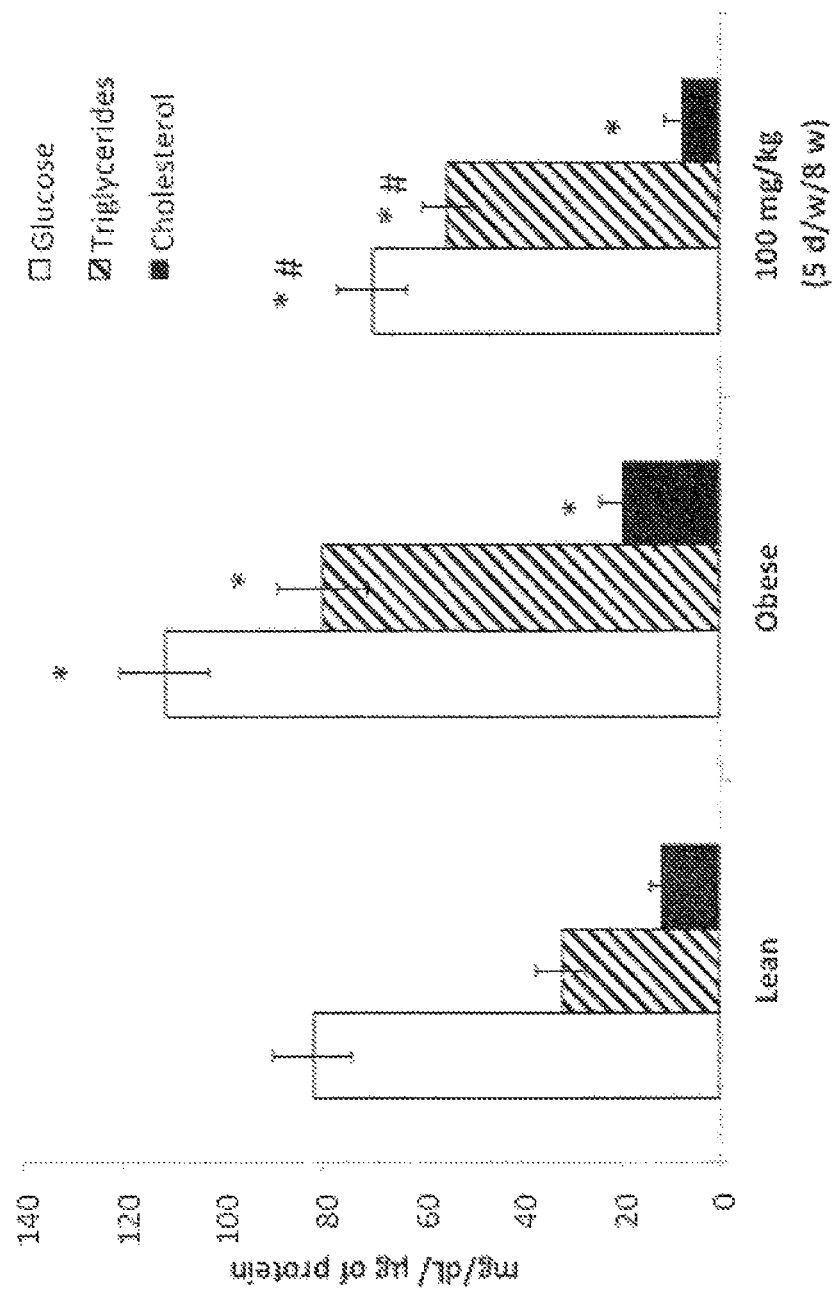
FIG. 10 is a bar graph showing the effect of (2R,3S)-(2-hydroxy-5-methyl-3-trimethylammonium-hexyl)-phosphonic acid dimethyl ester; iodide (100 mg/kg) on glucose, triglycerides and cholesterol from obese (fa/fa) Zucker rats (ZDF) and lean rats treated for five weeks. * p<0.01 compared to control group.
Figure 11:
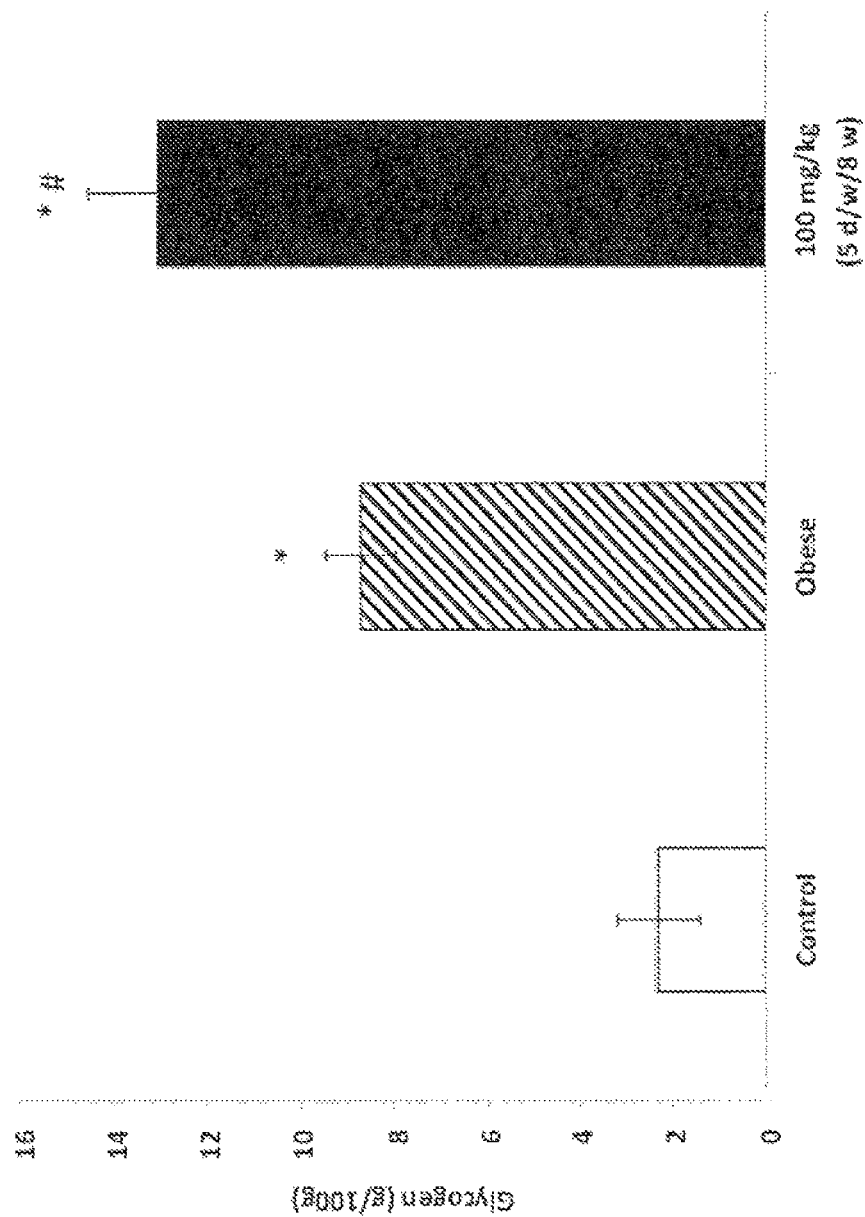
FIG. 11 is a bar graph showing the effect of (2R,3S)-(2-hydroxy-5-methyl-3-trimethylammonium-hexyl)-phosphonic acid dimethyl ester; iodide (100 mg/kg) on hepatic glycogen from obese (fa/fa) Zucker rats (ZDF) and lean rats treated for five weeks. * p<0.01 compared to control group.

It was found that rats treated with 100 mg/kg of Compound 2 produced a significant reduction in glucose, cholesterol, and triglycerides levels in the liver; glucose and cholesterol reached the control levels (FIG. 10; $p<0.01$). The amount of glycogen in the liver was higher in Compound 2 (100 mg/kg) treated Zucker rats (FIG. 11). Taken together, these data suggest that Compound 2 can be used to treat various diseases, conditions, or disorders in a subject, e.g., hepatitis, nonalcoholic fatty liver disease, fibrosis, and cirrhosis.

EXAMPLE 9

Cell Proliferation of THP-1 Cells

Figure 12:
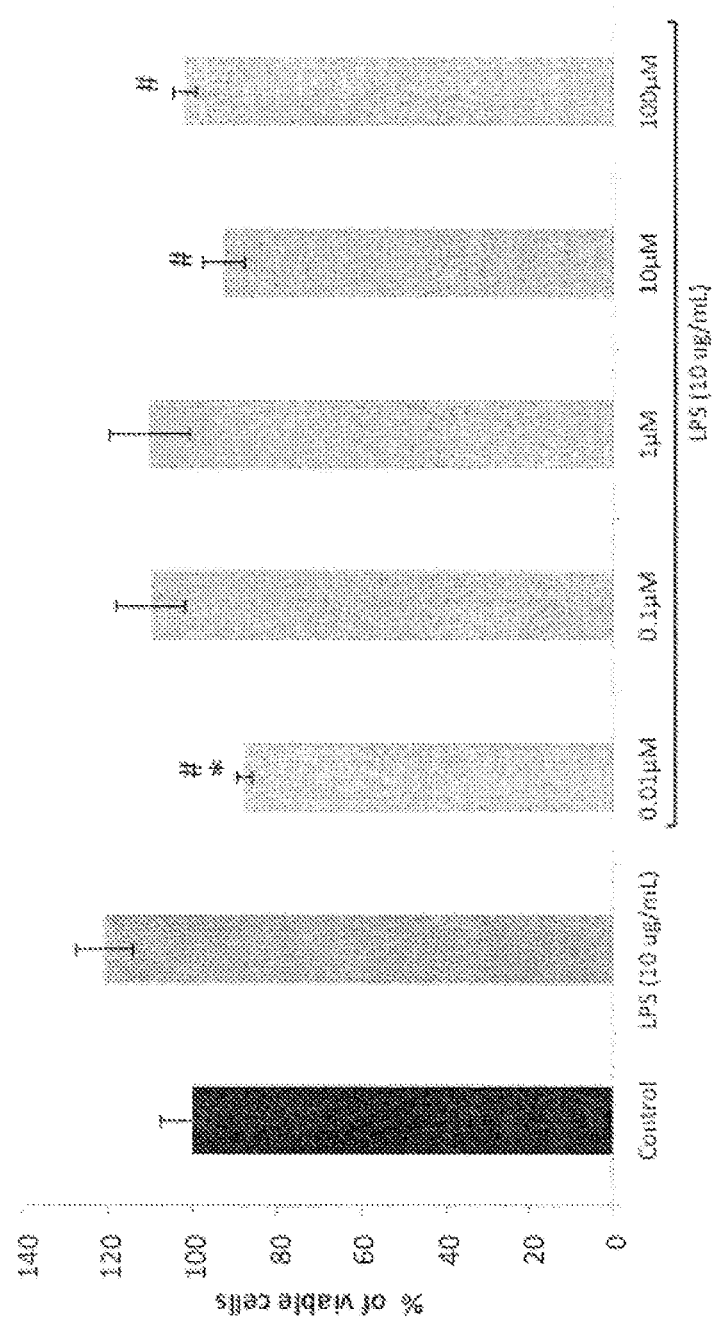
FIG. 12 is a bar graph showing the effect of (2R,3S)-(2-hydroxy-5-methyl-3-trimethylammonium-hexyl)-phosphonic acid dimethyl ester; iodide at different concentrations on cell proliferation of monocytic cells (THP-1 cells) co-stimulated with lipopolysaccharide (LPS, 10 μg/mL)* p<0.05 compared to control group. # p<0.05 as compared with LPS group.

The ability of (2R,3S)-(2-hydroxy-5-methyl-3-trimethyl-ammonium-hexyl)-phosphonic acid dimethyl ester iodide to modify the cell proliferation of monocytic cells (THP-1 cells) co-stimulated with lipopolysaccharide was investigated. THP-1 cells, a human monocytic cell line, were used and cultured in RPMI 1640 medium supplemented with 10% FBS and 100 U/ml penicillin-streptomycin. Cell cultures were incubated at 37° C. and 5% $CO_2$. THP-1 cells were plated at $1 \times 10^6$ cells/ml in 24-well microtiter plates. Cells were co-stimulated with lipopolysaccharide (LPS, 10 µg/mL) in order to induce cell proliferation. Cells were treated with the compound at different concentrations, and a reduction in the number of cells at 0.01, 10 and 100 µM at 24 hours of treatment were observed (FIG. 12).

Lipopolysaccharide or endotoxin, a major component of the outer surface of Gram-negative bacteria, is a potent activator of cells of the immune and inflammatory systems, including macrophages, monocytes, and endothelial cells. It is well known that lipopolysaccharide (LPS) induces human monocytes to express many proinflammatory mediators, including the procoagulant molecule tissue factor (TF) and the cytokine tumor necrosis factor alpha (TNF-α) leading to responses that are both protective and injurious to the host. The present results show that the compound (2R,3S)-(2-hydroxy-5-methyl-3-trimethylammonium-hexyl)-phosphonic acid dimethyl ester; iodide is able to inhibit the effect of LPS.

EXAMPLE 10

Cell Proliferation of THP-1 Cells

Figure 13:
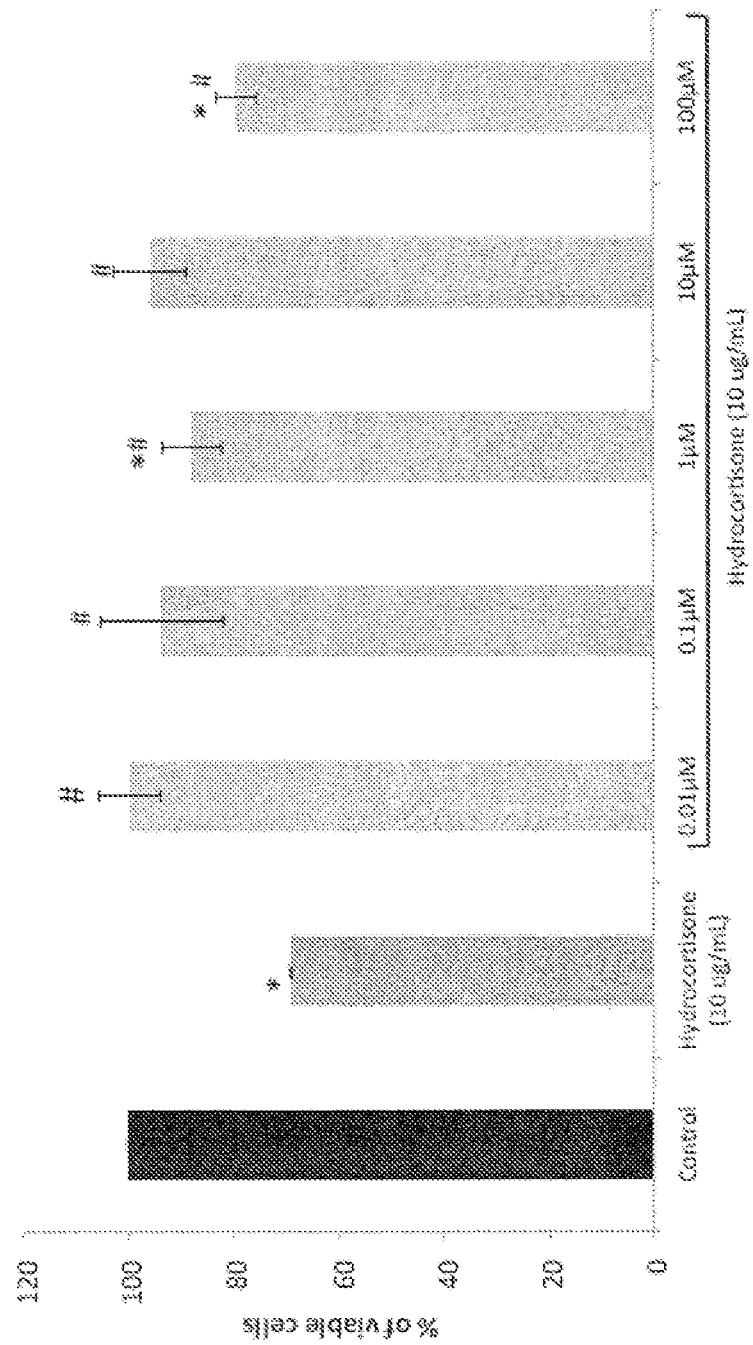
FIG. 13 is a bar graph showing the effect of (2R,3S)-(2-hydroxy-5-methyl-3-trimethylammonium-hexyl)-phosphonic acid dimethyl ester; iodide at different concentrations on cell proliferation of monocytic cells (THP-1 cells) co-inhibited with hydrocortisone (10 μg/mL)* p<0.05 compared to control group. # p<0.05 as compared with Hydrocortisone group.

The ability of (2R,3S)-(2-hydroxy-5-methyl-3-trimethyl-ammonium-hexyl)-phosphonic acid dimethyl ester; iodide to modify the cell proliferation of THP-1 cells was investigated. THP-1 cells were cultured in RPMI 1640 medium supplemented with 10% FBS and 100 U/ml penicillin-streptomycin. Cell cultures were incubated at 37° C. and 5% $CO_2$. THP-1 cells were plated at $1 \times 10^6$ cells/ml in 24-well microtiter plates. Cells were co-inhibited with hydrocortisone (10 µg/mL) to inhibit cell proliferation. When the cells were treated with the compound at different concentrations an induction of cell proliferation was observed with all used concentrations at 48 hours of treatment (FIG. 13).

Glucocorticoids modulate genes involved in the priming of the innate immune response, while their actions on the adaptive immune response are to suppress cellular [T helper (Th)1-directed] immunity and promote humoral (Th2-directed) immunity and tolerance. It is known that corticosteroids suppress the immune system via inhibition of the production of inflammatory cytokines and chemokines. Hydrocortisone, in particular, has been associated with an inhibition of cell proliferation by inhibit the cytokine production and NF-kB.

EXAMPLE 11

Phagocytic Activity of THP-1 Cells

Figure 14:
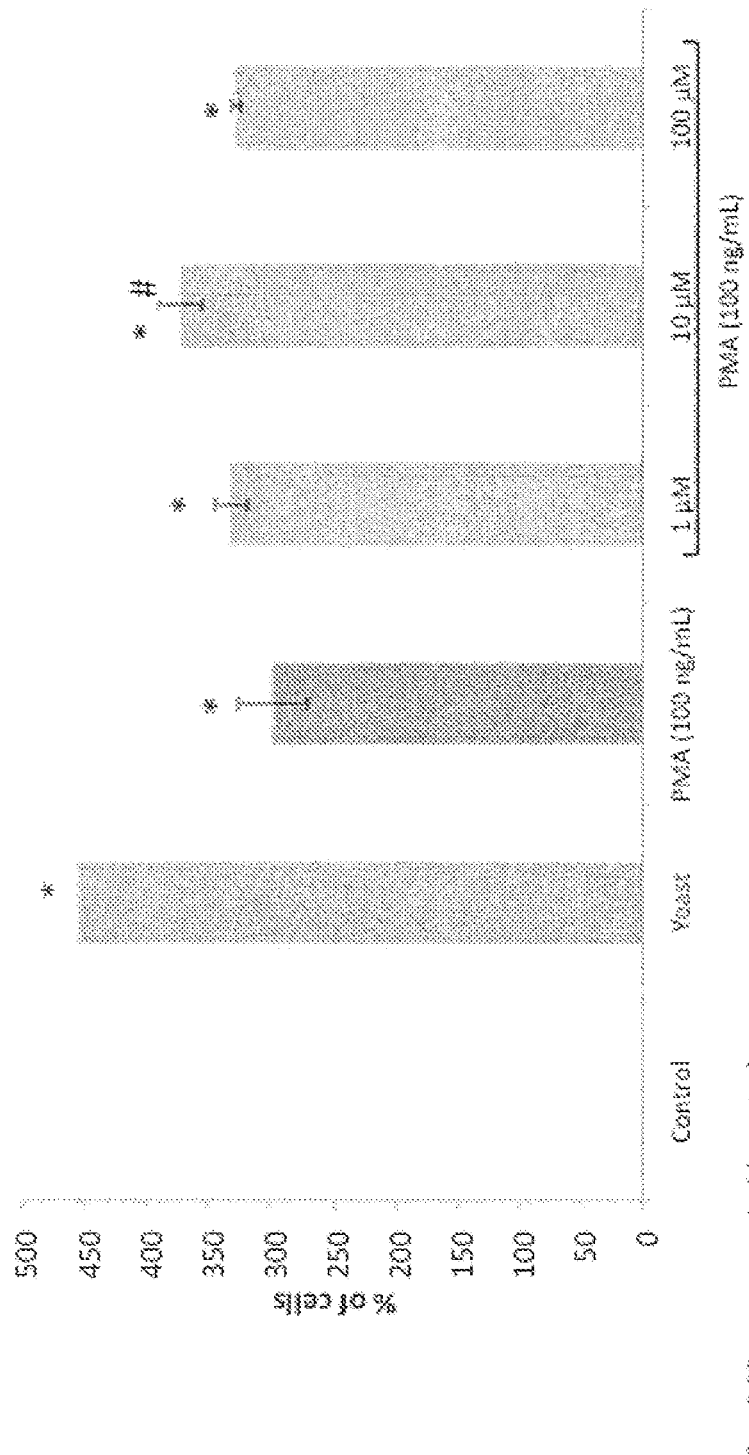
FIG. 14 is a bar graph showing the effect of (2R,3S)-(2-hydroxy-5-methyl-3-trimethylammonium-hexyl)-phosphonic acid dimethyl ester; iodide at different concentrations on phagocityc activity of macrophages. * p<0.05 compared to control group. # p<0.05 as compared with PMA group.
Figure 15:
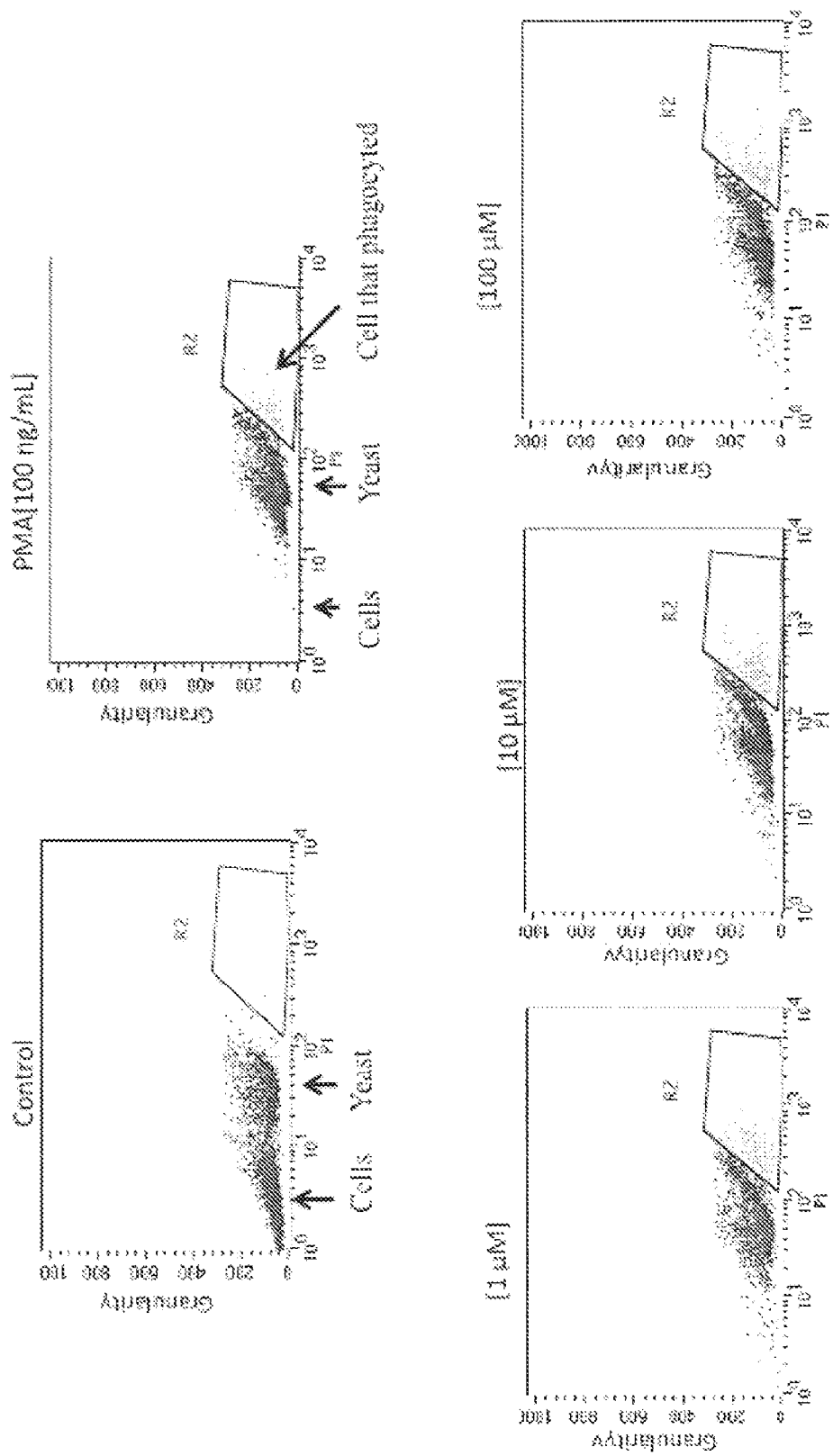
FIG. 15 is a flow cytometry graph showing the effect of (2R,3S)-(2-hydroxy-5-methyl-3-trimethylammonium-hexyl)-phosphonic acid dimethyl ester; iodide at different concentrations on phagocytic activity of macrophages.

The ability of (2R,3S)-(2-hydroxy-5-methyl-3-trimethyl-ammonium-hexyl)-phosphonic acid dimethyl ester; iodide to induce the phagocytic activity of monocytic cells (THP-1 cells) was investigated. For this, THP-1 cells were differentiated using phorbol myristate 13-acetate (PMA, 100 ng/mL) in order to induce the phagocytic activity of yeast. When the cells were treated with PMA (100 ng/mL) for 48 hours cell differentiation of monocytic cells to macrophages was observed (FIG. 14). Yeast were added to cultured media and the phagocytosis was measured by flow cytometry (FIG. 15). (2R,3S)-(2-hydroxy-5-methyl-3-trimethylammonium-hexyl)-phosphonic acid dimethyl ester; iodide induced the phagocytosis of yeast by macrophages in a similar way that those macrophages treated with PMA alone.

Phagocytosis of pathogens by macrophages initiates the innate immune response, which in turn orchestrates the adaptive response. In order to discriminate between infectious agents and self, macrophages have evolved a restricted number of phagocytic receptors, like the mannose receptor, that recognize conserved motifs on pathogens. Circulating monocytes play a major role in the immediate host response to invading microorganisms. The primary functions of monocytes include the phagocytosis of invading pathogens and the synthesis and secretion of proinflammatory cytokines, chemokines, and growth factors.

EXAMPLE 12

Reduction in Mycetoma Development

Figure 16:
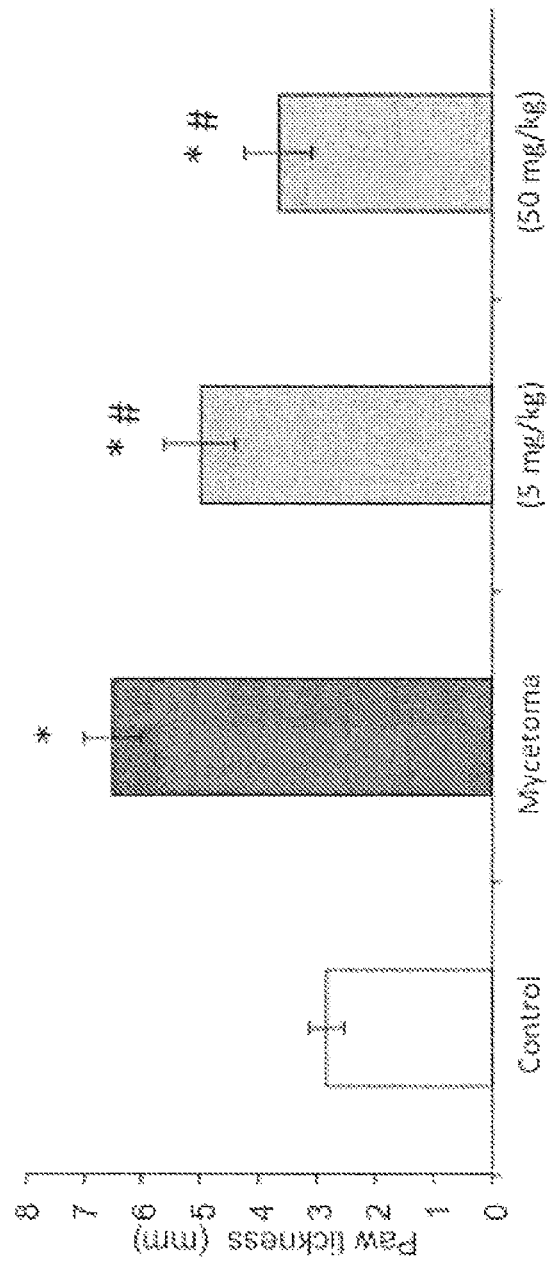
FIG. 16 is a bar graph showing the effect of (2R,3S)-(2-hydroxy-5-methyl-3-trimethylammonium-hexyl)-phosphonic acid dimethyl ester; iodide (5 and 50 mg/kg) on mycetoma induced in mice. * p<0.05 compared to mycetoma group.

The ability of (2R,3S)-(2-hydroxy-5-methyl-3-trimethyl-ammonium-hexyl)-phosphonic acid dimethyl ester; iodide at 5 mg/kg and 50 mg/kg to reduce the mycetoma development induced in mice was investigated. For this, male Balb-c mice weighing 25 grams were used. Mice were treated with dexamethasone (125 mg/kg) and mycetoma was induced with the inoculation *Nocardia brasiliensis* ($15 \times 10^8$ cells, se) (FIG. 16).

Mycetoma is a chronic infectious disease that remains localized, involves cutaneous and subcutaneous tissue, fascia, and bone, and is noncontagious. The disease is characterized by tumefaction, draining sinuses, and the presence of sclerotia. The 31 fungi known to cause mycetoma are associated with soil and woody plants. A chronic, tumor-like deforming disease develops during subsequent years following the introduction of the etiologic agent via localized trauma. After 15 days of treatment with (2R,3S)-(2-hydroxy-5-methyl-3-trimethylammonium-hexyl)-phosphonic acid dimethyl ester; iodide at 5 mg/kg and 50 mg/kg, a significant reduction in the paw thickness in those animals treated was observed (FIG. 17).

The present disclosure has been described with reference to certain embodiments thereof. However, the scope of the disclosure is not limited to the embodiments described or exemplified. Workers of ordinary skill in the relevant arts will readily appreciate that other embodiments and examples can be practiced without departing from the scope of the present disclosure. All such variations are considered to be part of, and therefore encompassed by, the present disclosure.

All publications, patents, and patent applications mentioned or referenced in this specification are herein incorporated by reference to the same extent as if each individual publication, patent or patent application was specifically and individually indicated to be incorporated by reference.

What is claimed is:

1. A method of stimulating the production of T-lymphocytes in a subject having type 1 insulin-dependent diabetes mellitus, dermatitis, osteoarthritis, rheumatoid arthritis, or granulomatosis, the method comprising administering a compound selected from the group consisting of:

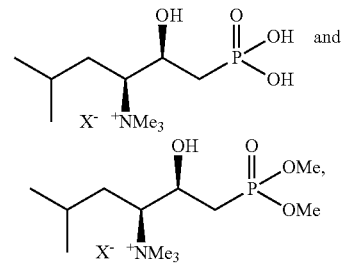

wherein:
$X^-$ is a pharmaceutically acceptable anion,
to said subject in an amount sufficient to stimulate the production of T-lymphocytes mellitus, osteoarthritis, arthritis or granulomatosis in said subject.

2. The method according to claim 1, wherein $X^-$ is iodide.

3. The method according to claim 1, wherein said compound is administered to said subject as part of a pharmaceutical composition comprising one or more pharmaceutically acceptable excipients.

4. The method according to claim 1, wherein said compound is:

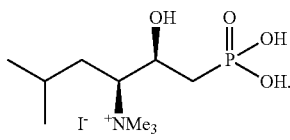

5. The method according to claim 1, wherein said compound is:

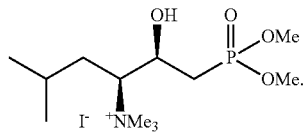

6. The method according to claim 1, wherein the subject has type 1 insulin-dependent diabetes mellitus.

7. The method according to claim 1, wherein the subject has dermatitis.

8. The method according to claim 1, wherein the subject has osteoarthritis.

9. The method according to claim 1, wherein the subject has rheumatoid arthritis.

10. The method according to claim 1, wherein the subject has granulomatosis.

* * * * *